United States Patent
Andersen

(10) Patent No.: US 10,858,642 B2
(45) Date of Patent: Dec. 8, 2020

(54) IMMUNOGENIC ARGINASE PEPTIDES

(71) Applicant: IO Biotech ApS, Copenhagen N (DK)

(72) Inventor: Mads Hald Andersen, Nærum (DK)

(73) Assignee: IO Biotech ApS, Copenhagen N (DK)

( * ) Notice: Subject to any disclaimer, the term of this patent is extended or adjusted under 35 U.S.C. 154(b) by 0 days.

(21) Appl. No.: 16/339,606

(22) PCT Filed: Oct. 6, 2017

(86) PCT No.: PCT/EP2017/075443
§ 371 (c)(1),
(2) Date: Apr. 4, 2019

(87) PCT Pub. No.: WO2018/065563
PCT Pub. Date: Apr. 12, 2018

(65) Prior Publication Data
US 2019/0338270 A1    Nov. 7, 2019

(30) Foreign Application Priority Data
Oct. 7, 2016    (EP) .................................... 16192794

(51) Int. Cl.
| | | |
|---|---|---|
| *C12N 9/78* | (2006.01) | |
| *A61P 35/00* | (2006.01) | |
| *A61K 39/00* | (2006.01) | |
| *A61K 45/06* | (2006.01) | |

(52) U.S. Cl.
CPC ........ *C12N 9/78* (2013.01); *A61K 39/001154* (2018.08); *A61K 45/06* (2013.01); *A61P 35/00* (2018.01); *C12Y 305/03001* (2013.01)

(58) Field of Classification Search
CPC ............ A61K 38/00; A61K 39/001154; A61K 45/06; A61P 35/00; C12N 9/78; C12N 9/96; C12Y 305/03001
See application file for complete search history.

(56) References Cited

U.S. PATENT DOCUMENTS

| | | |
|---|---|---|
| 2003/0228583 A1 | 12/2003 | Amacher et al. |
| 2012/0177628 A1* | 7/2012 | Georgiou ................ C12N 9/78 424/94.6 |
| 2013/0245237 A1 | 9/2013 | Rush et al. |

FOREIGN PATENT DOCUMENTS

| | | |
|---|---|---|
| EP | 0825260 | 2/1998 |
| WO | WO 2006/050313 | 5/2006 |
| WO | WO 2010051533 | 5/2010 |
| WO | WO 2016/102272 | 6/2016 |

OTHER PUBLICATIONS

Ahmad et al., "PD-L1 peptide co-stimulation increases immunogenicity of a dendritic cell-based cancer vaccine." in press ed. 2016.
Andersen et al. (1999) "Phosphorylated Peptides Can Be Transported by TAP Molecules, Presented by Class I MHC Molecules, and Recognized by Phosphopeptide-Specific CTL." J Immunol 163:3812-8.
Bronte & Zanovello, (2005) "Regulation of immune responses by L-arginine metabolism." Nat Rev Immunol 5:641-54.
Munder, "*Arginase: an emerging key player in the mammalian immune system.*" British Journal of Pharmacol. vol. 158, No. 3, 2009 pp. 638-651.
Mussai et al. (2013), "Acute myeloid leukemia creates an arginase-dependent immunosuppressive microenvironment." Blood 122:749-58.
Search Report, Singapore Application No. 11201902766R dated Jul. 13, 2020, 3 pages.

* cited by examiner

*Primary Examiner* — Marcela M Cordero Garcia
(74) *Attorney, Agent, or Firm* — Casimir Jones, S.C.; Melissa E. Kolom

(57) ABSTRACT

The present invention relates to immunogenic polypeptide fragments of a human Arginase protein. The fragments are in particular useful for the treatment or prevention of cancer.

29 Claims, 15 Drawing Sheets
Specification includes a Sequence Listing.

Figure 13

```
1: ARGI1_HUMAN   (SEQ ID NO: 1)
2: ARGI1_MOUSE   (SEQ ID NO: 59)
# Matrix: EBLOSUM62
# Gap_penalty: 10.0
# Extend_penalty: 0.5

# Length: 323
# Identity:     280/323 (86.7%)
# Similarity:   302/323 (93.5%)
# Gaps:           1/323 ( 0.3%)
# Score: 1480.0

ARGI1_HUMAN         1 MSAKSRTIGIIGAPFSKGQPRGGVEEGPTVLRKAGLLEKLKEQECDVKDY  50
                        ||:|.:::.||||||||||||||||:||..||||||||||.|.||:|:
  ARGI1_MOUSE         1 MSSKPKSLEIIGAPFSKGQPRGGVEKGPAALRKAGLLEKLKETEYDVRDH  50

ARGI1_HUMAN        51 GDLPFADIPNDSPFQIVKNPRSVGKASEQLAGKVAEVKKNGRISLVLGGD 100
                        |||.|.|:||||.|||||||||||||:|:|||.||||:||||:|:||||
  ARGI1_MOUSE        51 GDLAFVDVPNDSSFQIVKNPRSVGKANEELAGVVAEVQKNGRVSVVLGGD 100

ARGI1_HUMAN       101 HSLAIGSISGHARVHPDLGVIWVDAHTDINTPLTTTSGNLHGQPVSFLLK 150
                        ||||:|||||||||||||.||||||||||||||||:||||||||||||||
  ARGI1_MOUSE       101 HSLAVGSISGHARVHPDLCVIWVDAHTDINTPLTTSSGNLHGQPVSFLLK 150

ARGI1_HUMAN       151 ELKGKIPDVPGFSWVTPCISAKDIVYIGLRDVDPGEHYILKTLGIKYFSM 200
                        |||||.||||||||||||||||||||||||||||||||:|||||||||||
  ARGI1_MOUSE       151 ELKGKFPDVPGFSWVTPCISAKDIVYIGLRDVDPGEHYIIKTLGIKYFSM 200

ARGI1_HUMAN       201 TEVDRLGIGKVMEETLSYLLGRKKRPIHLSFDVDGLDPSFTPATGTPVVG 250
                        ||||:|||||||||||.|||||||||||||||||||||:|||||||||:|
  ARGI1_MOUSE       201 TEVDKLGIGKVMEETFSYLLGRKKRPIHLSFDVDGLDPAFTPATGTPVLG 250

ARGI1_HUMAN       251 GLTYREGLYITEEIYKTGLLSGLDIMEVNPSLGKTPEEVTRTVNTAVAIT 300
                        ||:||||||||||||||||||||||||||:||||.|||..||||||:|
  ARGI1_MOUSE       251 GLSYREGLYITEEIYKTGLLSGLDIMEVNPTLGKTAEEVKSTVNTAVALT 300

ARGI1_HUMAN       301 LACFGLAREGNHKP-IDYLNPPK     322
                        |||||..||||||| .|||.|||
  ARGI1_MOUSE       301 LACFGTQREGNHKPGTDYLKPPK     323
```

IMMUNOGENIC ARGINASE PEPTIDES

CROSS-REFERENCE TO RELATED APPLICATIONS

This application is a national phase application under 35 U.S.C. § 371 of PCT International Application No. PCT/EP2017/075443, filed Oct. 6, 2017, which claims priority to European Application No. 16192794.2, filed Oct. 7, 2016, each of which are hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 28,703 Byte ASCII (Text) file named "37700-US-1-PCT.TXT," created on Jun. 28, 2019.

TECHNICAL FIELD

The present invention relates to novel peptide compounds, such as fragments of Arginase 1, as well as compositions, uses, and kit-of-parts comprising these peptide compounds. Furthermore, the invention concerns nucleic acids, vectors, and host cells expressing said peptide compounds, for use in a method for treatment or prevention of a cancer, either alone or when administered simultaneously or sequentially with an additional cancer therapy.

BACKGROUND ART

Arginase is an enzyme that catalyses a reaction which converts the amino acid L-arginine into L-ornithine and urea. This depletes the microenvironment of arginine and leads to a suppression of tumor-specific cytotoxic T-cell responses. Increased Arginase activity has been detected in the cancer cells of patients with breast, lung, colon or prostate cancer [1]. It has been shown both in vitro and in vivo that mouse macrophages transfected with a rat Arginase gen promote the proliferation of co-cultured tumour cells [2]. Furthermore induction of Arginase expression by macrophages has been shown to increase tumour vascularization through polyamine synthesis. The results of a murine lung carcinoma model showed that there existed a subpopulation of mature tumor-associated myeloid cells that expressed high levels of Arginase. These tumor-associated myeloid cells depleted the extracellular L-Arginine which inhibited antigen-specific proliferation of the tumor infiltrating lymphocytes (TILs). Injection of an Arginase inhibitor blocked the growth of the lung carcinoma in the mice. This shows how induction of Arginase expression in tumor cells and tumor associated myeoloid cells might promote tumor growth by suppression of the anti-tumor immune responses through negative effects on TILs.

MDSCs (myeloid-derived suppressor cells) inhibit the activation, proliferation, and cytotoxicity of effector T cells and natural killer cells, as well as induce Treg differentiation and expansion. Both cancer cells and MDSCs can suppress T cells by manipulating L-arginine metabolism via the enzymes nitric-oxide synthase (NOS) and arginase. Many tumours exhibit increased expressions of arginase and inducible NOS (iNOS), leading to arginine depletion from the tumour microenvironment [1]. Several studies emphasize the importance of this altered tumour arginine metabolism in the suppression of tumour-specific T-cell responses, and it was recently demonstrated that AML blasts show an arginase-dependent ability to inhibit T-cell proliferation and hematopoietic stem cells. Furthermore, arginase and iNOS inhibitors reduce the suppressive activity of AML [2].

SUMMARY OF THE INVENTION

The present inventors have identified new immunogenic epitopes from Arginase 1. Furthermore, peripheral blood mononuclear cells (PBMC) from melanoma patients have been analysed for the presence of specific T-cell responses against Arginase 1-derived peptides and strong immune responses against the new immunogenic epitopes were detected. Moreover, frequent immune responses were detected against several peptide fragments. It has also been shown that the immune responses towards Arginase 1 indeed were mediated by CD4 and CD8 T cells, and that both CD8 and CD4 T cells can recognize Arginase 1 derived peptides on the surface of target cells.

The development of novel immune therapies for cancer requires a thorough understanding of the molecules that are involved in the pathogenesis as well as the specific proteins recognized by the immune system. In the clinical setting the induction of Arginase specific immune responses could in addition to the killing of cancer cells support anti-cancer immune responses in general by suppressing the immune suppressive function of Arginase expressing cells especially MDSC and tumor-associated macrophages (TAMs). Hence, since Arginase-expressing cells antagonize the desired effects of other immunotherapeutic approaches targeting myeloid dendritic cells e.g. by vaccination, would consequently be highly synergistic with additional anti-cancer immunotherapy.

Provided herein is an isolated, immunogenic polypeptide fragment of a human Arginase protein of SEQ ID NO: 1 (Arginase 1) or SEQ ID NO: 60 (Arginase 2). The fragment is typically up to 8, 9, 10, 15, 20, 25, 30, 45, 50 or 55 amino acids in length. The fragment may comprise or consists of a sequence of at least 8, 9, 10, 20, 30, 40 or 50 consecutive amino acids of either of SEQ ID NO: 52 or SEQ ID NO: 58. The polypeptide fragment may comprise or consist of the amino acid sequence of any one of SEQ ID NOs: 52, 50, 51, 34, 35, 36, 37, 9, 53, 54, 2 to 33, or 38 to 49.

The polypeptide fragment may have one or more of the following additional features:
  a. the C terminal amino acid is replaced with the corresponding amide; and/or
  b. the L at the position corresponding to position 190 of SEQ ID NO: 1 is replaced with I; and/or
  c. the R at the position corresponding to position 205 of SEQ ID NO: 1 is replaced with K; and/or
  d. at least one additional moiety is attached to the N and/or C terminus, optionally wherein said additional moiety is a hydrophilic amino acid such as R or K; and/or
  e. lacks or has reduced arginase activity relative to the corresponding full length arginase.

Also provided is a composition comprising a said fragment, a pharmaceutically acceptable diluent or carrier, and optionally an adjuvant. Said composition or said fragment may be for use in a method of treating or preventing a disease or condition such as cancer, or for use in the manufacture of a medicament for treating or preventing a disease or condition such as cancer. Said composition may optionally be described as a vaccine. Also provided is a method of treating or preventing a disease or condition such as cancer, the method comprising administering said composition or said fragment to a subject in need thereof.

The polypeptide fragment may be interchangeably described herein as a peptide compound or a peptide.

In one aspect the present disclosure concerns a peptide compound of Arginase 1 selected from:
a) a peptide fragment of SEQ ID NO 1 consisting of a consecutive sequence of from 8 to 321 amino acids,
b) a functional homologue having at least 70%, 80%, 90%, or 95% identity to SEQ ID NO 1 or the peptide fragment of a), and
c) a functional analogue wherein at least one amino acid has been deleted, inserted and/or substituted in SEQ ID NO 1 or the peptide fragment of a),
and wherein the C-terminal amino acid of any one of a), b) or c) also comprises the amide; or a pharmaceutically acceptable salt thereof. In the above-mentioned context, "functional" means "capable of stimulating an immune response to the Arginase of SEQ ID NO: 1". The homologue b) and analogue c) preferably have reduced (or zero) arginase function.

In an embodiment the peptide compound is selected from a) a peptide fragment of SEQ ID NO 1 consisting of a consecutive sequence of from 8 to 321 amino acids, wherein the C-terminal amino acid also comprises the amide; or a pharmaceutically acceptable salt thereof. In a further embodiment the peptide fragment consists of a consecutive sequence in the range of from 8 to 300 amino acids, 8 to 250 amino acids, 8 to 200 amino acids, 8 to 150 amino acids, 8 to 120 amino acids, e.g. 10 to 100 amino acids, 20 to 80 ami-no acids, 30 to 60 amino acids, 40 to 50 amino acids. In a still further embodiment the peptide fragment of SEQ ID NO 1 is selected from the group consisting of ARG(1-310), ARG(1-301), ARG(1-291), ARG(11-322), ARG(21-322), ARG(30-322), ARG(40-322), ARG(11-310), ARG(11-301), ARG(11-291), ARG(21-310), ARG(21-301), ARG(21-291), ARG(30-310), ARG(30-301), ARG(30-291), ARG(40-310), ARG(40-301), and ARG(40-291).

In a further embodiment the arginase activity is reduced compared to Arginase 1 as measured by an arginase activity assay. In one embodiment the arginase activity is reduced to inactivity. In another embodiment the arginase activity assay is selected from the Arginase Activity Colorimetric Assay Kit (BioVision Arginase assay # K755-100).

In a still further embodiment the consecutive sequence comprises one or more sequences selected from any one of SEQ ID NOs: 52, 50, 51, 37, 36, 35, 34, 9, 53, 54, 2 to 33, or 38 to 39. In one embodiment the consecutive sequence comprises the sequence selected from SEQ ID NO 52, 50, 51, 37, 36, 35, 34, 9, 53 or 54.

In a further embodiment the peptide fragment under a), the functional homologue under b), or the functional analogue under c) is functional in the sense that it activates T cells that recognizes Arginase 1 expressing cells. In one embodiment the activation is determined by the ELISPOT assay described herein.

Also disclosed herein is a nucleic acid encoding the peptide compound of the present invention. The peptide compound of the present invention is selected from any one of the above embodiments. In one embodiment the nucleic acid is selected from the group consisting of DNA and RNA.

Also disclosed herein is a vector comprising the nucleic acid of the present invention. The nucleic acid of the present invention is selected from any one of the above embodiments, and the peptide compound of the present invention is selected from any one of the above embodiments. In one embodiment the vector is selected from a virus vector.

In a further aspect the present disclosure relates to a host cell comprising the vector of the present invention. The vector is selected from any one of the above embodiments, the nucleic acid is selected from any one of the above embodiments, and the peptide compound is selected from any one of the above embodiments. In one embodiment the host cell is selected from a mammalian cell.

The vector preferably comprises a nucleic acid encoding an inactive sequence of Arginase 1, that is a sequence which lacks arginase function.

Any peptide, nucleic acid, vector, or host cell described herein may be provided in a composition, optionally together with a pharmaceutically acceptable additive, such as a carrier or diluent. The composition may optionally also comprise an adjuvant. The composition may be for use as a medicament. The composition may be for use in the manufacture of a medicament for treating or preventing a disease.

The composition may be for use in a method for treatment or prevention of a disease, disorder or condition selected from cancer. In one embodiment the cancer is a tumor forming cancer disease. The adjuvant may be selected from the group consisting of bacterial DNA based adjuvants, oil/surfactant based adjuvants, viral dsRNA based adjuvants, imidazochinilines, and a Montanide ISA adjuvant.

A method of treatment or prevention of a disease as disclosed herein may comprise administering to a subject an effective amount of:
a) a composition as described above, and
b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathio-prine, Bleomycin, Carboplatin, Capecitabine, Cisplatin, Chlorambucil, Cyclophospha-mide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotec-an, Lenalidomide, Leucovorin, Mechlorethamine, Melphalan, Mercaptopurine, Metho-trexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine, or a checkpoint inhibitor, e.g. antibody such as nivolumab or pembrolizumab.

In The provided compositions may be administered simultaneously or sequentially. The compositions may be provided as components in a kit-of-parts.

In a further aspect the present disclosure relates to a method of treating a clinical condition characterized by expression of Arginase 1 of SEQ ID NO 1, the method comprising administering to an individual suffering from said clinical condition an effective amount of the peptide, the nucleic acid, the vector or the host cell described above.

In a further aspect the present disclosure relates to a method of stimulation of arginase 1 specific T-cells, such as CD4 and CD8 T-cells, in a cancer patient, the method comprising administering to the cancer patient an effective amount of the peptide compound, or the nucleic acid, or the vector, or the host cell as described above.

In a still further aspect the present disclosure relates to a method of suppressing an immune suppressive function of Arginase 1 expressing cells, in a cancer patient, the method comprising administering to the cancer patient an effective amount of the peptide compound, or the nucleic acid, or the vector, or the host cell as described above.

In a further aspect the present disclosure relates to use of the peptide compound, or the nucleic acid, or the vector, or the host cell, as described above for the manufacture of a medicament, such as an immunotherapeutic composition or vaccine, for the treatment or prevention of a cancer, wherein said cancer is optionally characterized by expression of Arginase 1.

In a still further aspect the present disclosure relates to the peptide compound, or the nucleic acid, or the vector, or the host cell, for use in a method for treatment or prevention of a cancer, optionally when administered simultaneously or sequentially with an additional cancer therapy.

The additional cancer therapy may be selected from the group consisting of a cytokine therapy, a T-cell therapy, an NK therapy, an immune system checkpoint inhibitor, chemotherapy, radiotherapy, immunostimulating substances, gene therapy, antibodies and dendritic cells. In one embodiment the additional cancer therapy is selected from an immune system checkpoint inhibitor, such as a checkpoint blocking antibody (e.g. selected from nivolumab or pemrbolizumab), or is selected from the group consisting of Actimide, Azacitidine, Azathioprine, Bleomycin, Carboplatin, Capecitabine, Cisplatin, Chlorambucil, Cyclophosphamide, Cytarabine, Dauno-rubicin, Docetaxel, Doxifluridine, Doxorubicin, Epirubicin, Etoposide, Fludarabine, Fluor-ouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine.

B—Left: Responses against Arg(161-190) peptide in PBMCs from 5 selected cancer patients and four healthy donors. Right: Exemplary ELISPOT wells for responses against Arg(161-190) peptide or control in 2 healthy donors (HD.) and 2 cancer patients (MM.).

C—Left: Responses against Arg(181-210) peptide in PBMCs from 5 selected cancer patients and four healthy donors. Right: Exemplary ELISPOT wells for responses against Arg(161-190) peptide in 2 healthy donors (HD.) and 2 cancer patients (MM.).

Spot counts are given as a difference between averages of the wells stimulated with the peptide and control wells. Peptide and control stimulations were performed in triplicates.

Figure 11:
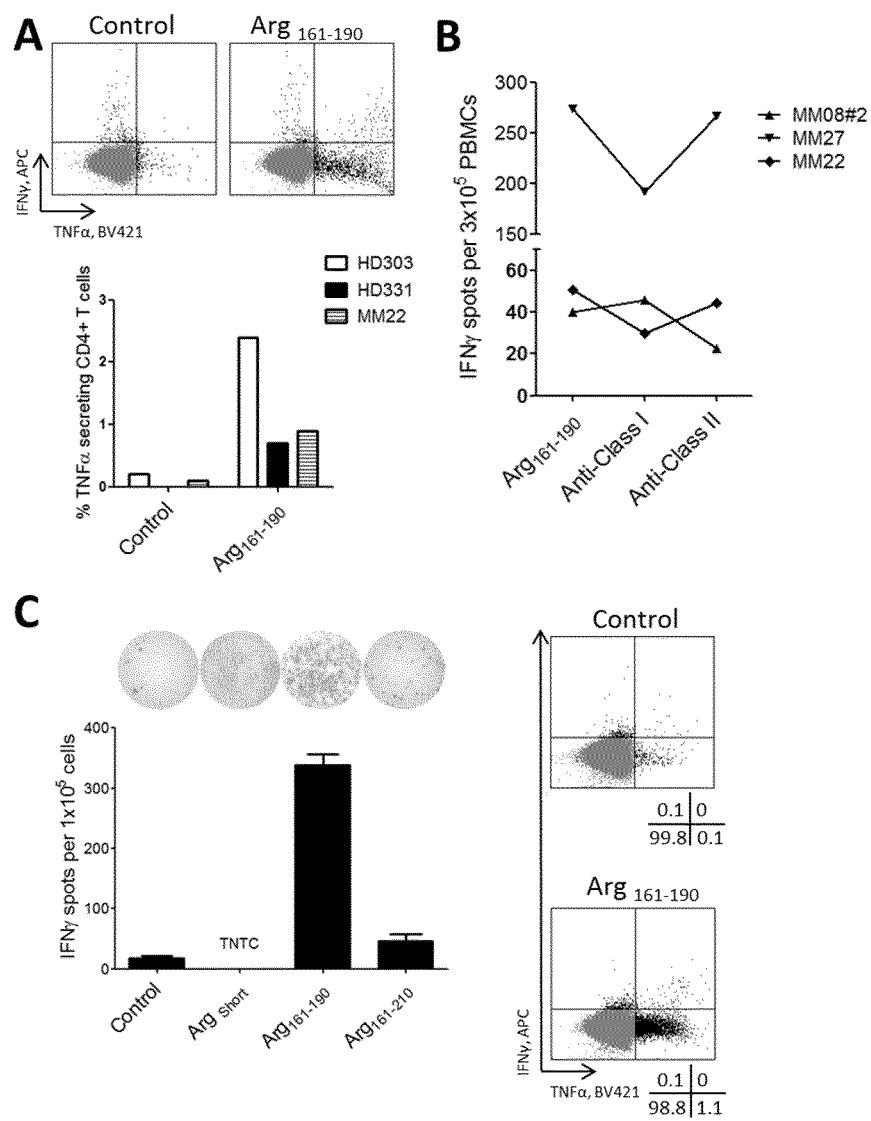

FIG. 11 shows further analysis of responses to the region corresponding to positions 161 to 210 of SEQ ID NO: 1

A—Top shows exemplary flow cytometry analysis of CD4 Tcells from a cancer patient, assessed by intracellular staining for IFN-g (PE-Cy7A) and TNF-alpha (APC-A) release following 8 hour stimulation with the peptide Arg(161-190) or unstimulated without peptide. Bottom shows the proportion TNF-a releasing CD4+ T cells in this assay for 2 healthy donors (HD.) and 1 cancer patient (MM.).

B—summary of IFNγ ELISPOT results following stimulation of PBMCs from 3 cancer patients with the peptide Arg(161-190) alone, or with antibody blocking of expression of HLA Class I (anti-Class I; W6/32) or HLA Class II (anti-Class II; Tü39). Spot counts are given as a difference between the wells stimulated with the peptide and control wells. Peptide and control stimulations were performed in duplicates or triplicates.

C—Left: IFNγ ELISPOT responses from Arginase specific CD4 T cells (produced by repeated stimulation with the peptide consisting of the amino acid sequence of SEQ ID NO: 9 (ArgShort)) when stimulated with ArgShort, the 30mer consisting of the sequence from positions 161 to 190 of Arginase 1 (Arg 161-190), or the 50mer consisting of the sequence from positions 161 to 210 of Arginase 1 (Arg 161-210), or when unstimulated (control). Right: Exemplary flow cytometry analysis of the Arginase specific CD4 T cells assessed by intracellular staining for IFN-g (PE-Cy7A) and TNF-alpha (APC-A) release following 8 hour stimulation with the peptide Arg(161-190) or control.

Figure 12:
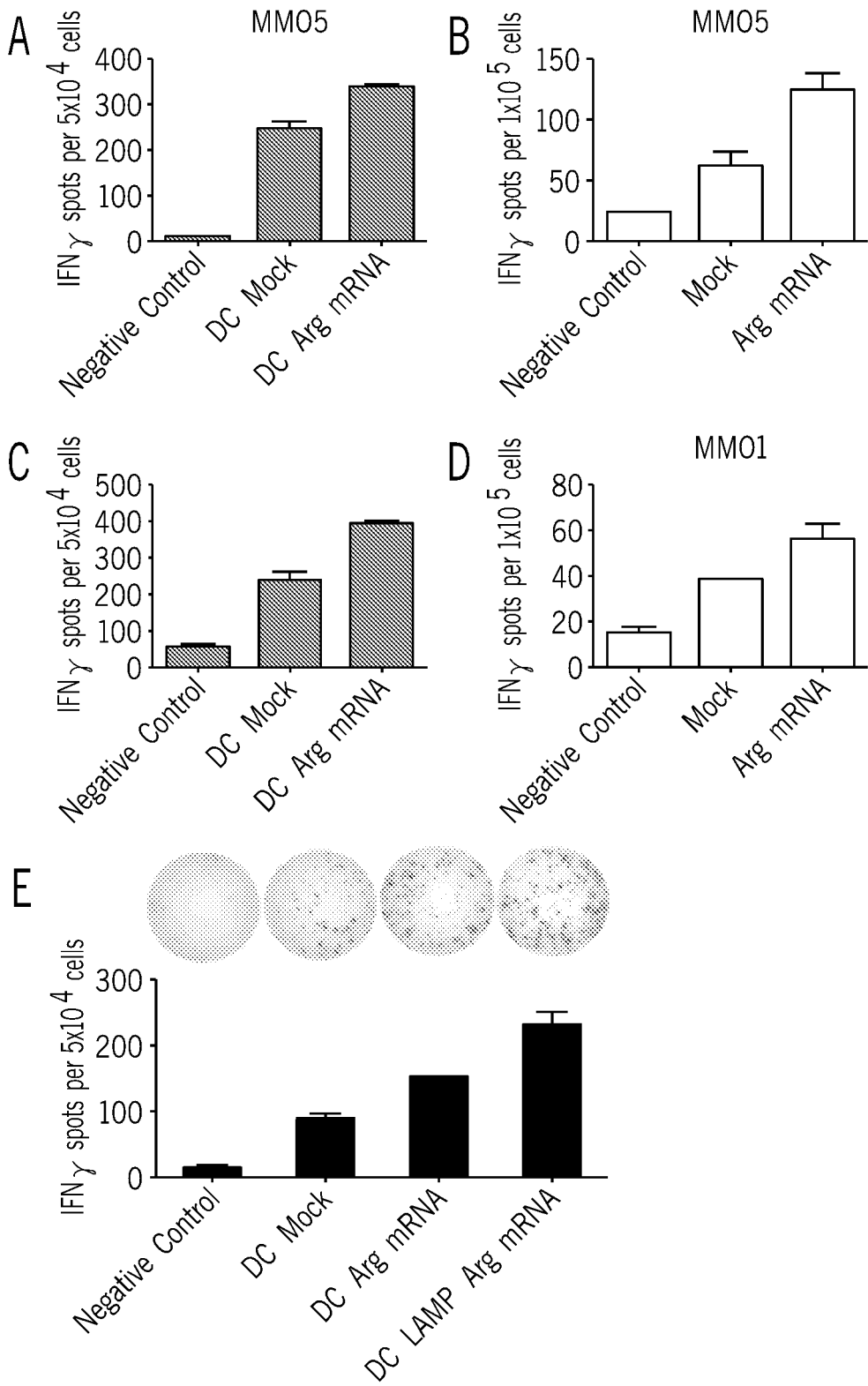

FIG. 12 shows Arginase-specific T cells recognize arginase-expressing immune cells A and C—IFNγ response by the arginase specific T cell cultures from two different melanoma patients (MM01 and MM05) to autologous dendritic cells electroporated and transfected with irrelevant control mRNA (DC Mock) or Arginase-1 mRNA (DC Arg mRNA). Effector to target ratio 10:1.

B and D—IFNγ response by the arginase specific T cell cultures from two different melanoma patients to autologous B cells electroporated and transfected with irrelevant control mRNA (DC Mock) or Arginase-1 mRNA (DC Arg mRNA) Effector to target 2:1.

E—Bottom: IFNγ response by arginase specific T cell culture towards autologous dendritic cells electroporated and transfected with irrelevant control mRNA (DC Mock), arginase mRNA (DC Arg mRNA) or arginase mRNA containing DC-LAMP signal sequence (DC LAMP Arg mRNA). Top: representative ELISPOT well images. Control and transfected cell stimulations were performed in duplicates or triplicates.

FIG. 13 is a sequence alignment of human Arginase 1 (SEQ ID NO: 1) and murine Arginase 1 (SEQ ID NO: 59).

Figure 14:
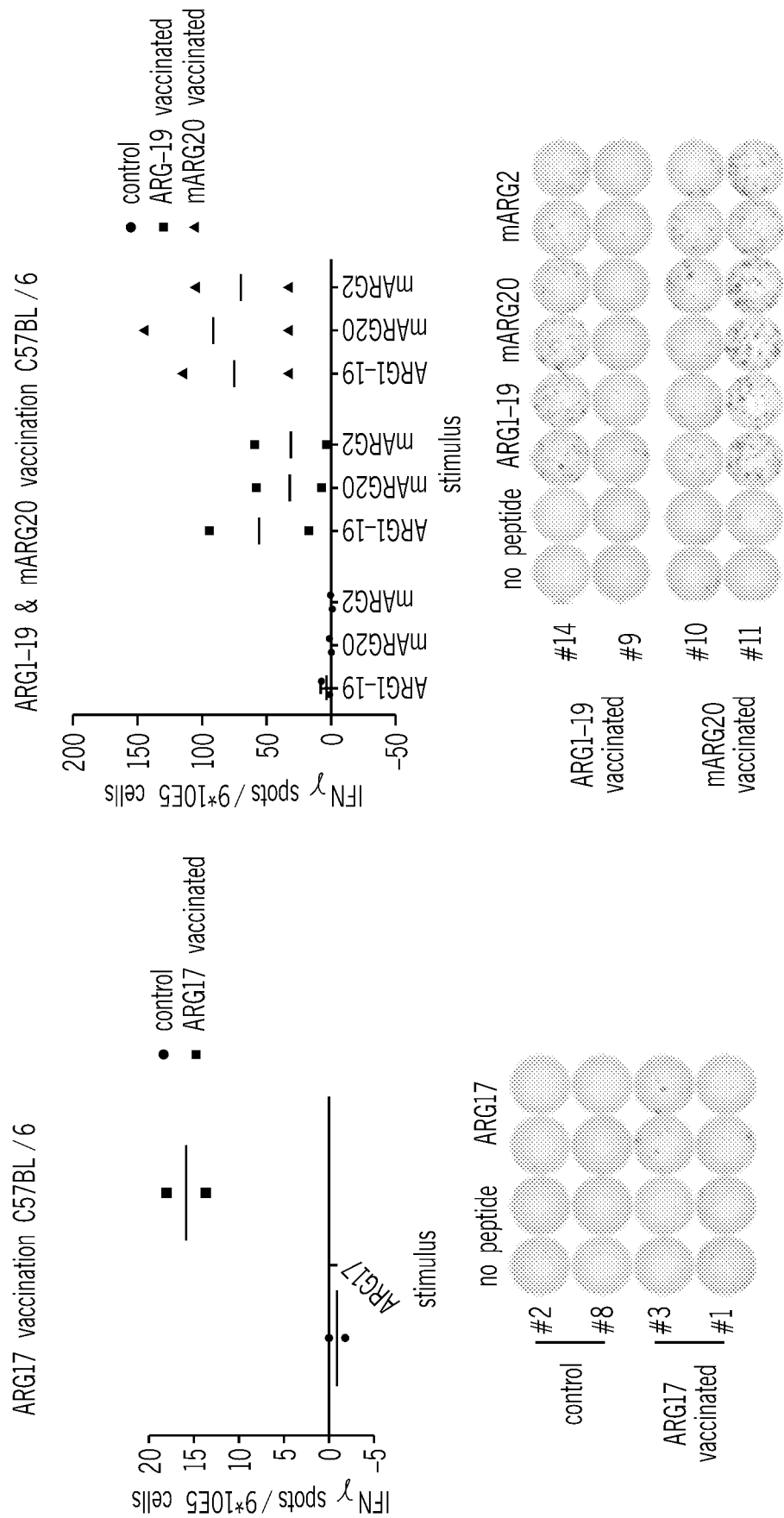

FIG. 14 shows that arginase specific immune responses are increased in C57BL/6 mice following vaccination with different peptides disclosed herein.

Figure 15:
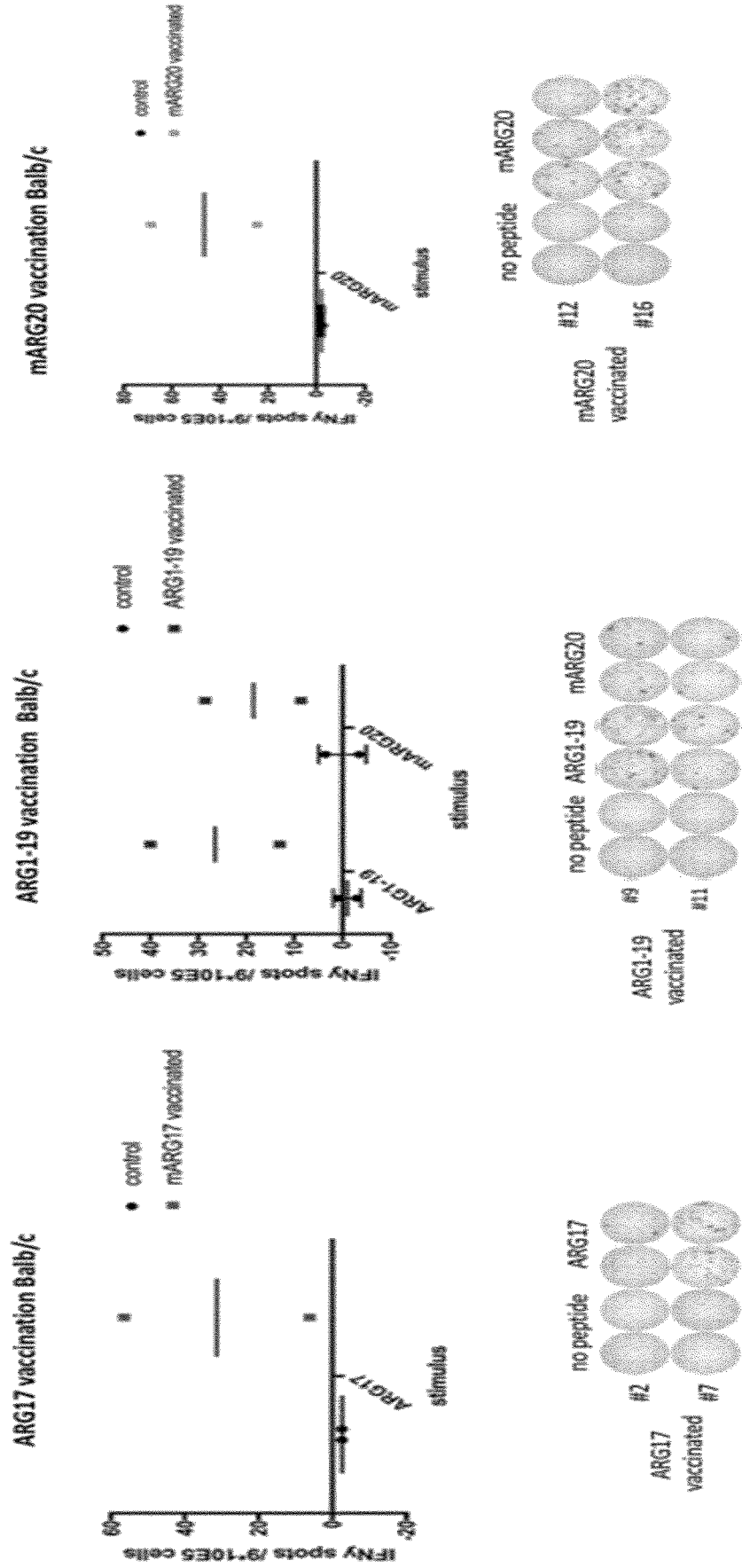

FIG. 15 shows that arginase specific immune responses are increased in Balb/c mice following vaccination with different peptides disclosed herein.

Figure 16:
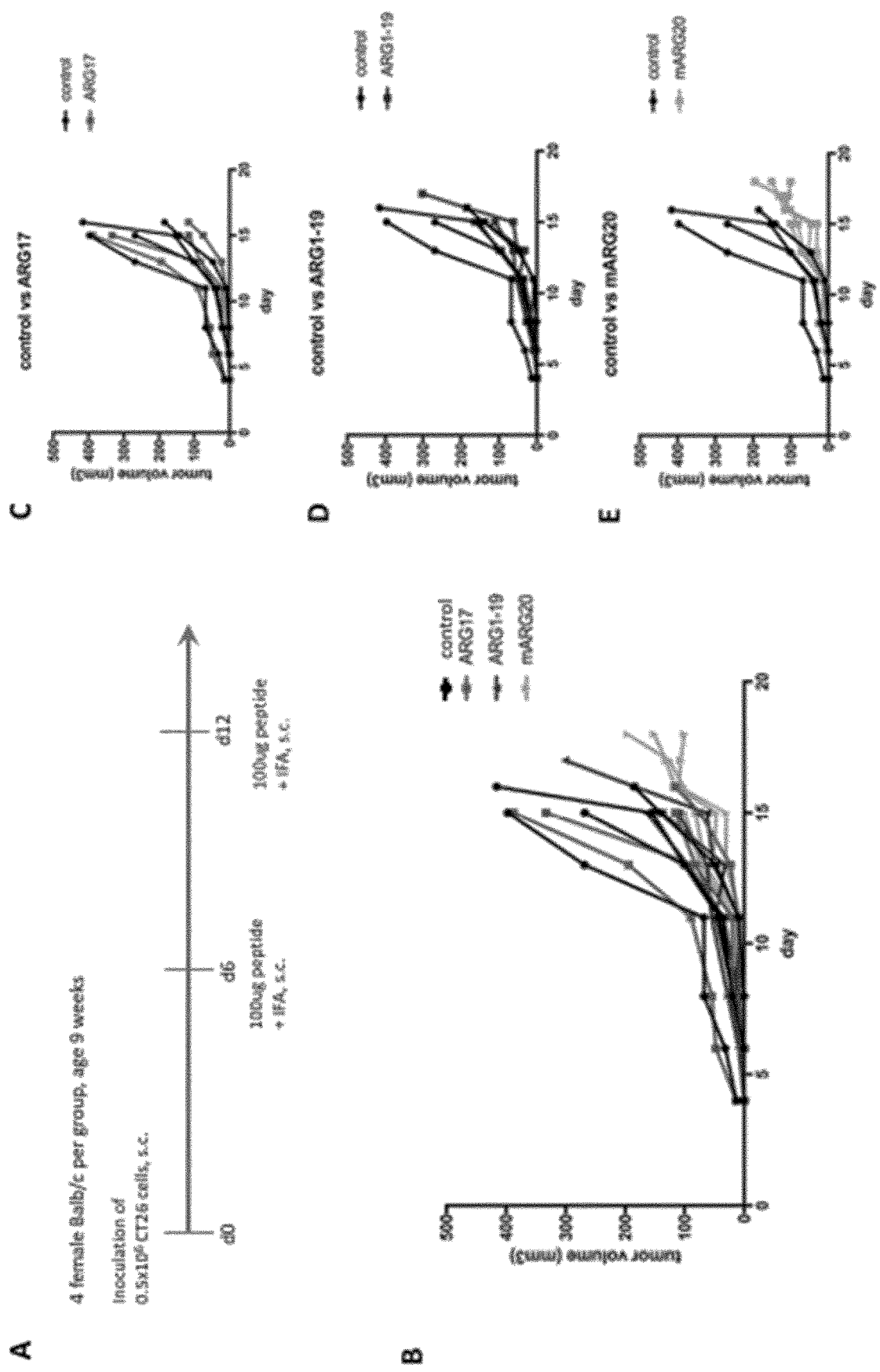

FIG. 16 shows reduction in tumour volumes in a mouse model of cancer vaccination with different peptides disclosed herein.

BRIEF DESCRIPTION OF SEQUENCES

SEQ ID NO: 1 is the wild type amino acid sequence of human Arginase 1
SEQ ID NOS: 2 to 54 are the amino acid sequences of peptide fragments of human Arginase 1
SEQ ID NOs: 55 to 57 are the amino acid sequences of peptide fragments of murine Arginase 1
SEQ ID NOs: 58 is the amino acid sequence of a peptide fragment of human Arginase 2
SEQ ID NO: 59 is the wild type amino acid sequence of murine Arginase 1
SEQ ID NO: 60 is the wild type amino acid sequence of human Arginase 2
SEQ ID NO: 61 is an alternative sequence of human Arginase 1

DETAILED DESCRIPTION OF THE INVENTION

The present invention is concerned with immunogenic polypeptide fragments of Arginase proteins. Such fragments may be useful as vaccines. By "immunogenic" it is meant that a polypeptide fragment is capable of eliciting an immune response, preferably a T-cell response, in at least one individual after administration to said individual. A polypeptide may be identified as immunogenic using any suitable method, including in vitro methods. For example, a peptide may be identified as immunogenic if it has at least one of the following characteristics:

(i) It is capable of eliciting IFN-γ-producing cells in a PBL population of at least one cancer patient as determined by an ELISPOT assay, and/or
(ii) It is capable of in situ detection in a sample of tumor tissue of CTLs that are reactive with the corresponding arginase; and/or
(iii) It is capable of inducing the in vitro growth of specific T-cells.

Methods suitable for determining whether a polypeptide is immunogenic active are also provided in the Examples section below.

The inventors have determined that multiple regions of the Arginase 1 sequence of SEQ ID NO: 1 are immunogenic. These include SEQ ID NOs: 52, 50, 51, 37, 36, 35, 34, 9, 53, 54, 2 to 33, or 38 to 49. SEQ ID NO: 52 corresponds to the region of Arginase1 from position 161 to 210 of SEQ ID NO: 1. This region may be described as a hotspot for immunogenicity because it comprises sequences against which T cell responses are detected most frequently amongst cancer patients and healthy subjects. The immunogenic polypeptide may be upto 50 or 55 amino acids in length and/or comprise at least 8, 9, 10, 15, 20, 25, 30, 35, 40, 45 or all 50 consecutive amino acids of SEQ ID NO: 52. Said consecutive amino acids may preferably comprise or consist of any one of SEQ ID NOs: 50, 51, 34, 35, 36, 37, 9, 53 and 54. Each of SEQ ID NOs: 50, 51, 34, 35, 36, 37, 9, 53 and 54 comprises sequences from within the sequence of SEQ ID NO: 52. Specifically, each of SEQ ID NOs: 50, 51, 34, 35, 36, 37, 9, 53 and 54 corresponds to the regions of SEQ ID NO: 1 defined by positions 161-190, 181-210, 161-180, 171-190, 181-200, 191-210, 174-182, 172-179 and 193-200, respectively.

The immunogenic polypeptide fragment may be upto 30, 35, 40, 45, 50 or 55 amino acids in length and comprise at least 8, 9, 10, 15, 20, 25 or all 30 consecutive amino acids of SEQ ID NO: 50 or 51. The immunogenic polypeptide fragment may be upto 20, 25, 30, 35, 40, 45, 50 or 55 amino acids in length and comprise at least 8, 9, 10, 15 or all 20 consecutive amino acids of any one of SEQ ID NOs: 37, 36, 35, 34.

The polypeptide fragment preferably comprises at least 8, 9, 10, 15 or all 20 consecutive amino acids from the region defined by positions 181-200 of SEQ ID NO: 1 (that is SEQ ID NO: 36) or most preferably at least 8, 9, 10, 15 or all 20 consecutive amino acids from the region defined by positions 191-200 of SEQ ID NO: 1 (that is SEQ ID NO: 37). The polypeptide fragment may comprise at least 8, 9, 10, 15 or all 20 consecutive amino acids from the region defined by positions 161-180 of SEQ ID NO: 1 (that is SEQ ID NO: 34) or positions 171-190 of SEQ ID NO: 1 (that is SEQ ID NO: 35). In the former (SEQ ID NO: 34), the cysteine corresponding to position 168 may optionally be replaced by conservative substitution, e.g. to improve solubility or stability.

The immunogenic polypeptide fragment may be upto 8 or 9 amino acids in length and may comprise at least 8 or 9 consecutive amino acids of any one of SEQ ID NOs: 9, 53 or 54. The immunogenic polypeptide fragment may comprise or consist of the amino acid sequence of any one of SEQ ID NOs: 52, 50, 51, 34, 35, 36, 37, 9, 53, 54, 2 to 33, or 38 to 49.

The inventors also identified responses in sequences which correspond to other regions of SEQ ID NO: 1, including the regions defined by (or at least partially overlapping with) positions 221-240 (see SEQ ID NOs: 40, 7, 14); 271-290 (see SEQ ID NOs: 45, 8, 10, 11, 12); 111-130 (see SEQ ID NOs: 29); 1-20 (see SEQ ID NOs: 18); 61-80 (see SEQ ID NOs: 24); 131-150 (see SEQ ID NOs: 31, 4); 141-160 (see SEQ ID NOs: 32, 4); 51-70 (see SEQ ID NOs: 23); 151-170 (see SEQ ID NOs: 33, 4); 211-240 (see SEQ ID NOs: 39, 6); and 281-300 (see SEQ ID NOs: 46). The immunogenic polypeptide fragment may thus comprise at least 8, 9 or more consecutive amino acids from any one of these regions or sequences. The immunogenic polypeptide fragment may comprise or consist of the amino acid sequence of any one of these regions or sequences.

Human Arginase 2 is related to Arginase 1 and there are some similarities in sequence (see SEQ ID NO: 60 versus SEQ ID NO: 1, respectively). The regions of interest in Arginase 1 are thus also likely to be of interest in Arginase 2. Accordingly, any one of the sequences described in the preceding section may have any one or more amino acids replaced with the one or more amino acids in the corresponding positions in Arginase 2. The entirety of the said sequence may be replaced with the corresponding sequence in Arginase 2. The immunogenic polypeptide may comprise or consist of a sequence of SEQ ID NO: 60 which is defined by the positions in SEQ ID NO: 60 that correspond to the positions in SEQ ID NO: 1 of any one of SEQ ID NOs: 52, 50, 51, 34, 35, 36, 37, 9, 53, 54, 2 to 33, or 38 to 49. For example, the hotspot region defined by positions 161-210 of SEQ ID NO: 1 corresponds to positions 180-229 of SEQ ID NO: 60 which are represented herein as SEQ ID NO: 58. Thus, references to SEQ ID NO: 52 may be replaced by references to SEQ ID NO: 58. The immunogenic polypeptide may comprise at least 8, 9, or preferably at least 20 or 30 consecutive amino acids of SEQ ID NO: 58.

Human Arginase 1 is also highly similar to murine Arginase 1 (see SEQ ID NO: 59 versus SEQ ID NO: 1, respectively, plus FIG. 13). Accordingly, any one of the sequences described in the preceding section for human Arginase 1 may have any one or more amino acids replaced with the one or more amino acids in the corresponding positions in murine Arginase 1. The entirety of the said sequence may be replaced with the corresponding sequence in murine Arginase 1. The immunogenic polypeptide may comprise or consist of a sequence of SEQ ID NO: 59 which is defined by the positions in SEQ ID NO: 59 that correspond to the positions in SEQ ID NO: 1 of any one of SEQ ID NOs: 52, 50, 51, 34, 35, 36, 37, 9, 53, 54, 2 to 33, or 38 to 49. For example, the hotspot region defined by positions 161-210 of SEQ ID NO: 1 corresponds to positions 161-210 of SEQ ID NO: 59, which are represented herein as SEQ ID NO: 57. Thus, references to SEQ ID NO: 52 may be replaced by references to SEQ ID NO: 57. The immunogenic polypeptide may comprise at least 8, 9, or preferably at least 20 or 30 consecutive amino acids of SEQ ID NO: 57. In effect, this means that the L at the position corresponding to position 190 of SEQ ID NO: 1 may be replaced with I and/or that the R at the position corresponding to position 205 of SEQ ID NO: 1 is replaced with K, in any polypeptide fragment described herein which encompasses those residues.

In any polypeptide fragment described herein, the C terminal amino acid may optionally be replaced with the corresponding amide, to improve solubility and/or to aid with manufacture/isolation. Similarly, the polypeptide may have attached at the N and/or C terminus at least one additional moiety to improve solubility and/or to aid with manufacture/isolation. Suitable moieties include hydrophilic amino acids. For example, the amino acids KR may be added at the N terminus and/or the amino acids RK may be added in order at the C terminus.

Any polypeptide fragment described herein preferably has reduced arginase activity relative to the corresponding full-length arginase. A reduction in arginase activity may include the reduction to inactivity. A suitable assay for arginase activity is the Arginase Activity Colorimetric Assay Kit (BioVision Arginase assay # K755-100).

In one aspect the present disclosure concerns a peptide compound of Arginase 1 selected from:
a) a peptide fragment of SEQ ID NO 1 consisting of a consecutive sequence of from 8 to 321 amino acids,
b) a functional homologue having at least 70%, 80%, 90%, or 95% identity to SEQ ID NO 1 or the peptide fragment of a), and c) a functional analogue wherein at least one amino acid has been deleted, inserted and/or substituted in SEQ ID NO 1 or the peptide fragment of a),
and wherein the C-terminal amino acid of any one of a), b) or c) also comprises the amide; or a pharmaceutically acceptable salt thereof.

In an embodiment the peptide compound is selected from b) a functional homologue having at least 70%, 80%, 90%, or 95% identity to SEQ ID NO 1 or the peptide fragment of a), wherein the C-terminal amino acid also comprises the amide; or a pharmaceutically acceptable salt thereof. In one embodiment the functional homologue has at least 80% identity to SEQ ID NO 1. In a further embodiment the functional homologue has at least 90% identity to SEQ ID NO 1. In a further embodiment the functional homologue has at least 95% identity to SEQ ID NO 1. In a further embodiment the functional homologue has at least 70% identity to the peptide fragment of a). In a further embodiment the functional homologue has at least 80% identity to the peptide fragment of a). In a further embodiment the functional homologue has at least 90% identity to the peptide fragment of a). In a further embodiment the functional homologue has at least 95% identity to the peptide fragment of a).

In another embodiment the peptide compound is selected from c) a functional analogue wherein at least one amino acid has been deleted, inserted and/or substituted in SEQ ID NO 1 or the peptide fragment of a), wherein the C-terminal amino acid also comprises the amide; or a pharmaceutically acceptable salt thereof.

In a further embodiment the peptide compound is selected from a) a peptide fragment of SEQ ID NO 1 consisting of a consecutive sequence of from 8 to 321 amino acids, wherein the C-terminal amino acid also comprises the amide; or a pharmaceutically acceptable salt thereof. In a further embodiment the peptide fragment consists of a consecutive sequence in the range of from 8 to 300 amino acids. In a further embodiment the peptide fragment consists of a consecutive sequence in the range of from 8 to 250 amino acids. In a further embodiment the peptide fragment consists of a consecutive sequence in the range of from 8 to 200 amino acids. In a further embodiment the peptide fragment consists of a consecutive sequence in the range of from 8 to 150 amino acids. In a further embodiment the peptide fragment consists of a consecutive sequence in the range of from 8 to 120 amino acids. In a further embodiment the peptide fragment consists of a consecutive sequence in the range of from 10 to 100 amino acids. In a further embodiment the peptide fragment consists of a consecutive sequence in the range of from 20 to 80 amino acids. In a further embodiment the peptide fragment consists of a consecutive sequence in the range of from 30 to 60 amino acids. In a further embodiment the peptide fragment consists of a consecutive sequence in the range of from 40 to 50 amino acids. In a still further embodiment the peptide fragment of SEQ ID NO 1 is selected from the group consisting of ARG(1-310), ARG(1-301), ARG(1-291), ARG(11-322), ARG(21-322), ARG(30-322), ARG(40-322), ARG(11-310), ARG(11-301), ARG(11-291), ARG(21-310), ARG(21-301), ARG(21-291), ARG(30-310), ARG(30-301), ARG(30-291), ARG(40-310), ARG(40-301), and ARG(40-291). In a still further embodiment the peptide fragment of SEQ ID NO 1 is selected from ARG(1-310). In a still further embodiment the peptide fragment of SEQ ID NO 1 is selected from ARG(1-301). In a still further embodiment the peptide fragment of SEQ ID NO 1 is selected from ARG(1-291). In a still further embodiment the peptide fragment of SEQ ID NO 1 is selected from ARG(11-322). In a still further embodiment the peptide fragment of SEQ ID NO 1 is selected from ARG(21-322). In a still further embodiment the peptide fragment of SEQ ID NO 1 is selected from ARG(30-322). In a still further embodiment the peptide fragment of SEQ ID NO 1 is selected from ARG(40-322). In a still further embodiment the peptide fragment of SEQ ID NO 1 is selected from ARG(11-310). In a still further embodiment the peptide fragment of SEQ ID NO 1 is selected from ARG(11-301). In a still further embodiment the peptide fragment of SEQ ID NO 1 is selected from ARG(11-291). In a still further embodiment the peptide fragment of SEQ ID NO 1 is selected from ARG(21-310). In a still further embodiment the peptide fragment of SEQ ID NO 1 is selected from ARG(21-301). In a still further embodiment the peptide fragment of SEQ ID NO 1 is selected from ARG(21-291). In a still further embodiment the peptide fragment of SEQ ID NO 1 is selected from ARG(30-310). In a still further embodiment the peptide fragment of SEQ ID NO 1 is selected from ARG(30-301). In a still further embodiment the peptide fragment of SEQ ID NO 1 is selected from ARG(30-291). In a still further embodiment the peptide fragment of SEQ ID NO 1 is selected from ARG(40-310). In a still further embodiment the peptide fragment of SEQ ID NO 1 is selected from ARG(40-301). In a still further embodiment the peptide fragment of SEQ ID NO 1 is selected from ARG(40-291). In a still further embodiment the peptide fragment of SEQ ID NO 1 is selected from ARG(161-190). In a still further embodiment the peptide fragment of SEQ ID NO 1 is selected from ARG(181-210). In a still further embodiment the peptide fragment of SEQ ID NO 1 is selected from ARG(161-210).

It is to be understood that when the peptide fragment consists of a consecutive sequence in the range of from 8 to 120, it may at the same time be selected within the sequence of for instance ARG(40-291), whereas a peptide fragment consisting of a consecutive sequence in the range of from 8 to 321, cannot be at the same time be selected within the sequence of for instance ARG(40-291), this is known to the person skilled in the art. Otherwise all combinations are contemplated within the present invention.

It is also to be understood that ARG(x-y), wherein x and y are integers selected from 1-322 as used herein means a peptide fragment of Arginase 1 having the SEQ ID NO 1 as defined herein, wherein x is the N-terminal amino acid and y is the C-terminal amino acid, for instance ARG(174-182) indicates the peptide fragment from amino acid 174 of SEQ ID NO 1 to amino acid 182 of SEQ ID NO 1 wherein amino acid 174 is I and amino acid 182 is V.

The term "identity" as used herein refers to a relationship between the sequences of two or more peptides, such as polypeptides, as determined by comparing the sequences. In the art, "identity" also means the degree of sequence relatedness between proteins or polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins or peptides can be readily calculated by known methods. Such methods include, but are not limited to, those described in Computational Molecular Biology, Lesk, A. M., ed., Oxford University Press, New York, 1988; Biocomputing: Informatics and Genome Pro-jects, Smith, D. W., ed., Academic Press, New York, 1993; Computer Analysis of Sequence Data, Part 1, Griffin, A. M., and Griffin, H. G., eds., Humana Press, New Jersey, 1994; Se-quence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48, 1073, (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res., 12, 387, (1984); Genetics Computer Group, University of Wisconsin, Madison, Wis.), BLASTP, BLASTN, and FASTA (Altschul et al., J. Mol. Biol., 215, 403-410, (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two proteins for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA, 89, 10915-10919, (1992) for the BLOSUM 62 comparison matrix) is also used by the algorithm. Preferred parameters for a protein or peptide sequence comparison include the following: Algorithm: Needleman et al., J. Mol. Biol, 48, 443-453, (1970); Comparison matrix: BLOSUM 62 from Henikoff et al., Proc. Natl. Acad. Sci. USA, 89, 10915-10919, (1992); Gap Penalty: 12, Gap Length Penalty: 4, Threshold of Similarity: 0. The GAP program is useful with the above parameters. The aforementioned parameters are the default parameters for protein comparisons (along with no penalty for end gaps) using the GAP algorithm.

In a further embodiment the arginase activity is reduced compared to Arginase 1 as measured by an arginase activity assay. In one embodiment the arginase activity is reduced to inactivity. In another embodiment the arginase activity assay is selected from the Arginase Activity Colorimetric Assay Kit (BioVision Arginase assay # K755-100). In a further embodiment the arginase activity is reduced to inactivity compared to Arginase 1 as measured by the arginase activity assay is selected from the Arginase Activity Colorimetric Assay Kit.

In a still further embodiment the consecutive sequence comprises one or more sequences selected from any one of SEQ ID NO 2-17. In one embodiment the consecutive sequence comprises the sequence selected from SEQ ID NO 9. In another embodiment the consecutive sequence comprises only the sequence selected from SEQ ID NO 9, but not any one of the SEQ ID NO 2-8 or 10-17.

In a further embodiment the consecutive sequence comprises the sequence having SEQ ID NO 50. In a still further embodiment the consecutive sequence comprises the sequence having SEQ ID NO 51. In a further embodiment the consecutive sequence comprises the sequence having SEQ ID NO 52.

In a further embodiment the peptide fragment under a), the functional homologue under b), or the functional analogue under c) activates T cells that recognizes Arginase 1 expressing cells. In one embodiment the activation is determined by the ELISPOT assay described herein. In a further embodiment the peptide fragment under a), activates T cells that recognizes Arginase 1 expressing cells as determined by the ELISPOT assay described herein.

In a particular aspect the disclosure concerns a peptide compound of Arginase 1 selected from:
a) SEQ ID NO 52 or a peptide fragment of SEQ ID NO 52 consisting of a consecutive sequence having from 8 to 49 amino acids,
b) a functional homologue having at least 70%, 80%, 90%, or 95% identity to SEQ ID NO 52 or the peptide fragment of a), and
c) a functional analogue wherein at least one amino acid has been deleted, inserted and/or substituted in SEQ ID NO 52 or the peptide fragment of a),
and wherein the C-terminal amino acid of any one of a), b) or c) also comprises the amide; or a pharmaceutically acceptable salt thereof. It is intended that any one of the peptide compounds of a), b) or c) can be the subject of individual embodiments.

In a further embodiment the peptide fragment consists of a consecutive sequence in the range of from 9 to 49 amino acids, such as from 10 to 40 amino acids, such as from 20 to 30 amino acids.

In a further embodiment the peptide fragment of SEQ ID NO 52 consisting of a consecutive sequence having from 8 to 49 amino acids, comprises the SEQ ID NO 51. In a further embodiment the peptide fragment of SEQ ID NO 52 consisting of a consecutive sequence having from 8 to 49 amino acids, comprises the SEQ ID NO 50. In a further embodiment the peptide fragment of SEQ ID NO 52 consisting of a consecutive sequence having from 8 to 49 amino acids, comprises the SEQ ID NO 9.

In a further embodiment the peptide fragment comprises at least one CD4+ and at least one CD8+ T cell epitope. In a still further embodiment the peptide fragment comprises at least one CD4+ or at least one CD8+ T cell epitope. In a further embodiment the peptide fragment comprises at least one CD4+ T cell epitope. In a still further embodiment the peptide fragment comprises at least one CD8+ T cell epitope. In a further embodiment the peptide fragment comprises all T cell epitopes, in particular all CD4+ and CD8+ epitopes, located in a hot-spot region in ARG(161-210). In a still further embodiment the peptide fragment comprises all T cell epitopes except one, in particular all CD4+ and CD8+ epitopes, located in a hot-spot region in ARG(161-210).

In a further aspect the disclosure relates to a nucleic acid encoding the peptide compound of the present invention. The peptide compound is selected from any one of the above embodiments. In one embodiment the nucleic acid is selected from the group consisting of DNA and RNA.

In a still further aspect the disclosure relates to a vector comprising the nucleic acid of the present invention. The nucleic acid is selected from any one of the above embodiments, and the peptide compound of the present invention is selected from any one of the above embodiments. In one embodiment the vector is selected from a virus vector.

In a further aspect the present disclosure relates to a host cell comprising the vector of the present invention. The vector is selected from any one of the above embodiments, the nucleic acid is selected from any one of the above embodiments, and the peptide compound is selected from any one of the above embodiments. In one embodiment the host cell is selected from a mammalian cell.

In a still further aspect the disclosure relates to a vector comprising a nucleic acid encoding an inactive sequence of Arginase 1 selected from:
a) a peptide fragment of SEQ ID NO 1 consisting of a consecutive sequence of from 8 to 321 amino acids,
b) a functional homologue having at least 70%, 80%, 90%, or 95% identity to SEQ ID NO 1 or the peptide fragment of a), and
c) a functional analogue wherein at least one amino acid has been deleted, inserted and/or substituted in SEQ ID NO 1 or the peptide fragment of a),
and wherein the C-terminal amino acid of any one of a), b) or c) also comprises the amide, wherein the nucleic acid expresses the inactive sequence, and wherein the inactive sequence comprises at least 1 immunogenic epitope. In one embodiment the epitope is selected from the group consisting of SEQ ID NO 2-17, typically the epitope is selected from SEQ ID NO 9. In another embodiment the epitope may comprise any sequence of at least 8 consecutive amino acids comprised within any one of SEQ ID NOs: 50-52.

In a further aspect the disclosure relates to a composition comprising the peptide compound or the nucleic acid or the vector or the host cell of the present disclosure, optionally together with a pharmaceutically acceptable additive, such as carrier or adjuvants.

In a still further aspect the present disclosure relates to an immunotherapeutic composition comprising
a) the peptide compound of the present invention or the nucleic acid of the present invention or the vector of the present invention or the host cell of the present invention; and
b) an adjuvant;
for use as a medicament.

In an embodiment the immunotherapeutic composition is for use in a method for treatment or prevention of a disease, disorder or condition selected from cancer. In one embodiment the cancer is a tumor forming cancer disease. In a further embodiment the adjuvant is selected from the group consisting of bacterial DNA based adjuvants, oil/surfactant based adjuvants, viral dsRNA based adjuvants, imidazochinilines, and a Montanide ISA adjuvant.

In a further aspect the present disclosure relates to a kit-of-parts comprising;
a) the immunotherapeutic composition of the present invention, and
b) a composition comprising at least one second active ingredient, selected from an immunostimulating compound, such as an interleukin, e.g. IL-2 and or IL-21, an anti-cancer agent, such as Actimide, Azacitidine, Azathio-prine, Bleomycin, Carboplatin, Capecitabine, Cisplatin, Chlorambucil, Cyclophospha-mide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotec-an, Lenalidomide, Leucovorin, Mechlorethamine, Melphalan, Mercaptopurine, Metho-trexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine.

In an embodiment of the kits-of-parts, the provided compositions are to be administered simultaneously or sequentially.

In a further aspect the disclosure relates to a method of treating a clinical condition characterized by expression of Arginase 1 of SEQ ID NO 1, the method comprising administering to an individual suffering from said clinical condition an effective amount of the peptide compound of the present invention or the nucleic acid of the present invention or the vector of the present invention or the host cell of the present invention.

In a further aspect the disclosure relates to a method of stimulation of arginase 1 specific T-cells, such as CD4 and CD8 T-cells, in a cancer patient, the method comprising administering to the cancer patient an effective amount of the peptide compound of, or the nucleic, or the vector, or the host cell of the disclosure.

In a still further aspect the present disclosure relates to a method of suppressing an immune suppressive function of Arginase 1 expressing cells, in a cancer patient, the method comprising administering to the cancer patient an effective amount of the peptide compound, or the nucleic acid, or the vector, or the host cell of the disclosure.

In a further aspect the disclosure relates to use of the peptide compound, or the nucleic acid, or the vector, or the host cell of the disclosure, for the manufacture of a medicament, such as an immunotherapeutic composition or vaccine, for the treatment or prevention of a cancer characterized by expression of Arginase 1.

In a still further aspect the disclosure relates to the peptide compound, or the nucleic acid, or the vector, or the host cell of the disclosure, for use in a method for treatment or prevention of a cancer, when administered simultaneously or sequentially with an additional cancer therapy.

The additional cancer therapy is selected from the group consisting of a cytokine therapy, a T-cell therapy, an NK therapy, an immune system checkpoint inhibitor, chemotherapy, radiotherapy, immunostimulating substances, gene therapy, anti-bodies and dendritic cells. In one embodiment the additional cancer therapy is selected from an immune system checkpoint inhibitor, such as a checkpoint blocking antibody (e.g nivolumab, pembrolizumab), or is selected from the group consisting of Actimide, Azacitidine, Azathioprine, Bleomycin, Carboplatin, Capecitabine, Cisplatin, Chlorambucil, Cyclophosphamide, Cytarabine, Dauno-rubicin, Docetaxel, Doxifluridine, Doxorubicin, Epirubicin, Etoposide, Fludarabine, Fluor-ouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine.

Arginase activity may be measured for instance by using the Arginase Activity Colorimetric Assay Kit (BioVision Arginase assay # K755-100). BioVision's Arginase Activity Assay kit is simple, sensitive and rapid. In this assay, Arginase reacts with arginine & undergoes a series of reactions to form an intermediate that reacts stoichiometrically with OxiRed™ Probe to generate the colored product (OD 570 nm). The kit can detect Arginase activity less than 0.2 U/L in 96-well assay format.

As used herein any amino acid sequence shown may be modified at the C-terminal amino acid to be in amide form (—CONH$_2$) or may be in acid form (—COOH), thus any one of these are preferred embodiments, and it is intended that any C-terminal amino acid, such as I, F, R, L, K, G, M, D, V, S, T, N, Y, P comprises both amide and acid forms unless specified by —NH$_2$ or —OH.

The arginase peptide fragments disclosed herein are made by standard peptide synthesis, such as solid-phase peptide synthesis (SPPS). SPPS is a standard method for synthesizing peptides in the lab. SPPS allows for the synthesis of natural peptides which are difficult to express in bacteria, the incorporation of unnatural amino acids, peptide/protein backbone modification, and the synthesis of D-proteins, which consist of D-amino acids. Small porous beads are treated with functional units ('linkers') on which peptide chains can be built. The peptide will remain covalently attached to the bead until cleaved from it by a reagent such as anhydrous hydrogen fluoride or trifluoroacetic acid. The peptide is thus 'immobilized' on the solid-phase and can be retained during a filtration process while liquid-phase reagents and by-products of synthesis are flushed away. The general principle of SPPS is one of repeated cycles of deprotection-wash-coupling-wash. The free N-terminal amine of a solid-phase attached peptide is coupled to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin. There are two majorly used forms of SPPS-Fmoc and Boc. Unlike ribosome protein synthesis, solid-phase peptide synthesis proceeds in a C-terminal to N-terminal fashion. The N-termini of amino acid monomers is protected by either of these two groups and added onto a deprotected amino acid chain. Automated synthesizers are available for both techniques, though many research groups continue to perform SPPS manually. Furthermore, the skilled person will understand that the processes described above and hereinafter the functional groups of intermediate compounds may need to be protected by protecting group.

When the peptide compounds, nucleic acids, vectors, host cells and pharmaceutical compositions herein disclosed are used for the above treatment, a therapeutically effective amount of at least one compound is administered to a mammal in need of said treatment.

As used herein amino acids are identified by the one or three letter code known to the person skilled in the art and shown in the table below for convenience:

| Amino acids, one and three letter codes | | |
| --- | --- | --- |
| Amino acid | Three letter code | One letter code |
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |

-continued

Amino acids, one and three letter codes

| Amino acid | Three letter code | One letter code |
|---|---|---|
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, monkeys, apes, sheep and pigs.

The term "a therapeutically effective amount" of a peptide compound of the present invention or a peptide fragment disclosed herein, as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the disclosure relates to a pharmaceutical composition comprising the peptide compound, such as peptide fragment, of the present invention and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the peptide compound, peptide fragment, nucleic acid, vector, or host cell and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

Adjuvants are any substance whose admixture into the composition increases or otherwise modifies the immune response elicited by the composition. Adjuvants, broadly defined, are substances which promote immune responses. Adjuvants may also preferably have a depot effect, in that they also result in a slow and sustained release of an active agent from the administration site. A general discussion of adjuvants is provided in Goding, Monoclonal Antibodies: Principles & Practice (2nd edition, 1986) at pages 61-63.

Adjuvants may be selected from the group consisting of: AlK(SO4)2, AlNa(SO4)2, AlNH4 (SO4), silica, alum, Al(OH)3, Ca3 (PO4)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+ TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum*, *Bordetella pertussis*, and members of the genus *Brucella*, Titermax, ISCOMS, Quil A, ALUN (see U.S. Pat. No. 58,767 and U.S. Pat. No. 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Various saponin extracts have also been suggested to be useful as adjuvants in immunogenic compositions. Granulocyte-macrophage colony stimulating factor (GM-CSF) may also be used as an adjuvant.

Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. GM-CSF and Imidazochinilines are also examples of preferred adjuvants.

The adjuvant is most preferably a Montanide ISA adjuvant. The Montanide ISA adjuvant is preferably Montanide ISA 51 or Montanide ISA 720.

In Goding, Monoclonal Antibodies: Principles & Practice (2nd edition, 1986) at pages 61-63 it is also noted that, when an antigen of interest is of low molecular weight, or is poorly immunogenic, coupling to an immunogenic carrier is recommended. A peptide compound, peptide fragment, nucleic acid, vector, or host cell of an immunotherapeutic composition of the invention may be coupled to a carrier. A carrier may be present independently of an adjuvant. The function of a carrier can be, for example, to increase the molecular weight of the peptide compound, peptide fragment, nucleic acid, vector, or host cell in order to increase activity or immunogenicity, to confer stability, to increase the biological activity, or to increase serum half-life. Furthermore, a carrier may aid in presenting the polypeptide or fragment thereof to T-cells. Thus, in the immunogenic composition, the polypeptide or fragment thereof may be associated with a carrier such as those set out below.

The carrier may be any suitable carrier known to a person skilled in the art, for example a protein or an antigen presenting cell, such as a dendritic cell (DC). Carrier proteins include keyhole limpet hemocyanin, serum proteins such as transferrin, bovine serum albumin, human serum albumin, thyroglobulin or ovalbumin, immunoglobulins, or hormones, such as insulin or palmitic acid. Alternatively, the carrier protein may be tetanus toxoid or diphtheria toxoid. Alternatively, the carrier may be a dextran such as sepharose. The carrier must be physiologically acceptable to humans and safe.

The immunotherapeutic composition may optionally comprise a pharmaceutically acceptable excipient. The excipient must be 'acceptable' in the sense of being compatible with the other ingredients of the composition and not deleterious to the recipient thereof. Auxiliary substances, such as wetting or emulsifying agents, pH buffering substances and the like, may be present in the excipient. These excipients and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

The immunotherapeutic composition may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. In one embodiment of a composition, the active ingredient is provided in dry (for e.g., a powder or granules) form for reconstitution with a suitable vehicle (e. g., sterile pyrogen-free water) prior to administration of the reconstituted composition. The composition may be prepared, packaged, or sold in the form of a sterile injectable aqueous or oily suspension or solution. This suspension or solution may be formulated according to the known art, and may comprise, in addition to the active ingredient, additional ingredients such as the adjuvants, excipients and auxiliary substances described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. Alternatively, the active ingredients of the composition may be encapsulated, adsorbed to, or associated with, particulate carriers. Suitable particulate carriers include those derived from polymethyl methacrylate polymers, as well as PLG microparticles derived from poly (lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

As mentioned above, the compositions and particularly immunotherapetic compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly immunotherapetic composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'immunotherapetic composition', 'peptide compound for use as a medicament', or 'peptide compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a peptide" includes two or more such peptides.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, amino acid analogs and peptidomimetics, and any pharmaceutically acceptable salts thereof.

A "subject" as used herein includes any mammal, preferably a human.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in herein to the maximum extent permitted by applicable law.

ASPECTS

The following are some additional aspects of the present disclosure:
1. A peptide compound of Arginase 1 selected from:
   a) a peptide fragment of SEQ ID NO 1 consisting of a consecutive sequence of from 8 to 321 amino acids,
   b) a functional homologue having at least 70%, 80%, 90%, or 95% identity to SEQ ID NO 1 or the peptide fragment of a), and
   c) a functional analogue wherein at least one amino acid has been deleted, inserted and/or substituted in SEQ ID NO 1 or the peptide fragment of a),
   and wherein the C-terminal amino acid of any one of a), b) or c) also comprises the amide; or a pharmaceutically acceptable salt thereof.
2. The peptide compound of aspect1 selected from a) a peptide fragment of SEQ ID NO 1 consisting of a consecutive sequence of from 8 to 321 amino acids, wherein the C-terminal amino acid also comprises the amide; or a pharmaceutically acceptable salt thereof.
3. The peptide compound of aspect2 wherein the peptide fragment consists of a consecutive sequence in the range of from 8 to 300 amino acids, 8 to 250 amino acids, 8 to 200 amino acids, 8 to 150 amino acids, 8 to 120 amino acids, e.g. 10 to 100 amino acids, 20 to 80 amino acids, 30 to 60 amino acids, 40 to 50 amino acids.
4. The peptide compound of any one of aspects 2-3 wherein the peptide fragment of SEQ ID NO 1 is selected from the group consisting of ARG(1-310), ARG(1-301), ARG(1-291), ARG(11-322), ARG(21-322), ARG(30-322), ARG(40-322), ARG(11-310), ARG(11-301), ARG(11-291), ARG(21-310), ARG(21-301), ARG(21-291), ARG(30-310), ARG(30-301), ARG(30-291), ARG(40-310), ARG(40-301), and ARG(40-291).
5. The peptide compound of any one of aspects 1-4 wherein the arginase activity is reduced compared to Arginase 1, preferably reduced to inactivity, as measured by an arginase activity assay, such as the Arginase Activity Colorimetric Assay Kit (BioVision Arginase assay # K755-100).
6. The peptide compound of any one of aspects 2-5 wherein the consecutive sequence comprises one or more sequences selected from any one of SEQ ID NO 2-17, such as one sequence selected from SEQ ID NO 9.
7. The peptide compound of any one of aspects 1-6 wherein the peptide fragment under a), the functional homologue under b), or the functional analogue under c) activates T cells that recognizes Arginase 1 expressing cells.
8. The peptide compound of aspect7 wherein the activation is determined by the ELISPOT assay described herein.
9. A nucleic acid, such as DNA or RNA, encoding the peptide compound of any one of the preceding aspects.
10. A vector, such virus vector, comprising the nucleic acid of aspect9.
11. A host cell, such as mammalian cell, comprising the vector of aspect10.
12. A vector comprising a nucleic acid encoding an inactive sequence of Arginase 1 selected from:
   a) a peptide fragment of SEQ ID NO 1 consisting of a consecutive sequence of from 8 to 321 amino acids,
   b) a functional homologue having at least 70%, 80%, 90%, or 95% identity to SEQ ID NO 1 or the peptide fragment of a), and
   c) a functional analogue wherein at least one amino acid has been deleted, inserted and/or substituted in SEQ ID NO 1 or the peptide fragment of a),
   and wherein the C-terminal amino acid of any one of a), b) or c) also comprises the amide, wherein the nucleic acid expresses the inactive sequence, and wherein the inactive sequence comprises at least 1 immunogenic epitope, such as an epitope selected from the group consisting of SEQ ID NO 2-17, typically the epitope is selected from SEQ ID NO 9.
13. A composition comprising the peptide compound of any one of aspects 1-8 or the nucleic acid of aspect 9 or vector of aspect10 or 12 or host cell of aspect11, optionally together with a pharmaceutically acceptable additive, such as carrier or adjuvants.
14. An immunotherapeutic composition comprising
    a) the peptide compound of any one of aspects 1-8 or the nucleic acid of aspect9 or vector of aspect10 or 12 or host cell of aspect11; and
    b) an adjuvant;
    for use as a medicament.
15. The immunotherapeutic composition of aspect14 for use in a method for treatment or prevention of a disease, disorder or condition selected from cancer, such as a tumor forming cancer disease.
16. The immunotherapeutic composition of any one of aspects 14-15 wherein the adjuvant is selected from the group consisting of bacterial DNA based adjuvants, oil/surfactant based adjuvants, viral dsRNA based adjuvants, imidazochinilines, a Montanide ISA adjuvant.
17. A kit-of-parts comprising;
    a) the immunotherapeutic composition of any one of aspects 14-16, and
    b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine.
18. The kits-of-parts according to aspect17, where the provided compositions are to be administered simultaneously or sequentially.
19. A method of treating a clinical condition characterized by expression of Arginase 1 of SEQ ID NO 1, the method comprising administering to an individual suffering from said clinical condition an effective amount of the peptide compound of any one of aspects 1-8 or the nucleic acid of aspect9 or vector of aspect10 or 12 or host cell of aspect 11.
20. A method of stimulation of arginase 1 specific T-cells, such as CD4 and CD8 T-cells, in a cancer patient, the method comprising administering to the cancer patient an effective amount of the peptide compound of any one of aspects 1-8 or the nucleic acid of aspect9 or vector of aspect10 or 12 or host cell of aspect 11.
21. A method of suppressing an immune suppressive function of Arginase 1 expressing cells, in a cancer patient, the method comprising administering to the cancer patient an effective amount of the peptide compound of any one of aspects 1-8 or the nucleic acid of aspect9 or vector of aspect10 or 12 or host cell of aspect 11.
22. Use of the peptide compound of any one of aspects 1-8 or the nucleic acid of aspect9 or vector of aspect10 or 12 or host cell of aspect 11 for the manufacture of a medicament, such as an immunotherapeutic composition or vaccine, for the treatment or prevention of a cancer characterized by expression of Arginase 1.
23. A peptide compound of any one of aspects 1-8 or the nucleic acid of aspect9 or vector of aspect10 or 12 or host cell of aspect 11, for use in a method for treatment or prevention of a cancer, when administered simultaneously or sequentially with an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells.
24. The peptide fragment, nucleic acid, vector or host cell of aspect23 wherein the checkpoint blocking antibodies are selected from Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXAMPLES

Introduction

The following explains the rationale behind the planning and execution of some of the following experiments:

In addition to the new immunogenic epitopes from Arginase 1, and strong immune responses against the new immunogenic epitopes as well as frequent immune responses detected against several peptide fragments of Arginase 1, the present inventor also will identify if T cells likewise recognize Arginase. Furthermore, immunogenic epitopes from Arginase will be identified. Using the reverse immunology approach, potential MHC class I binding motifs will be identified followed by the synthesis of candidate peptides. Subsequently, the actual binding to the corresponding MHC alleles will be established. Following the identification of class I binding peptide compounds, such peptides will be examined in an ELISPOT assay for cytokine release by peptide specific T cells in order to examine whether specific T cells are present among peripheral PBMC of cancer patients as well as healthy donors. In the planned study tetrameric MHC/-peptide-complexes will be used as additional means of investigating T-cell reactivity in peripheral blood by flow cytometry. Finally, tetrameric MHC/peptide complexes will be used to isolate specific T cells directly from patient blood or tumor infiltrated lymph nodes. This will be used determine the functional capacity of specific T cells.

Additionally, the inventor will search for novel epitopes presented by MHC class II molecules, since CD4+ T cells play a critical role in generating and maintaining antigen-specific cellular and humoral immune responses. CD4+ T cells are presented with 18-mer overlapping synthetic peptides spanning the entire protein sequence in ELISPOT assays. Peptide-specific CD4+ T-cell clones are generated by repetitive stimulation with peptide. Furthermore, using a set of partially histocompatible EBV-B cell lines and MHC class II-specific antibodies, the HLA class II restriction elements will be identified. Finally, tumor infiltrating lymphocytes (TIL) cultures will be analyzed for reactivity against CD4 and CD8 peptide epitopes revealing important information regarding pivotal in vivo targets.

Arginase is a major player in the immune system and is, it could be speculated that such T cells are involved in general immune regulation. An additional part of these studies aim at analysing the role of Arginase specific T cells may therefore also have a role in immune regulation. First, it will be examined if Arginase-specific T cells can effect immunity by eliminating arginase-expressing regulatory cells thereby suppressing and/or delaying local immune suppression. To examine a possible immune effect of Argiasese T cells, it will be examined if The presence of Arginase-specific T cells or the activation of such T cells by Arginase-derived peptides may boost additional T- and/or B-cell responses against other antigens. Regulatory cells contribute to the strength and duration of a given immune response. Thus, any "supportive" effect of Arginase-specific T cells on other immune cells may well be mediated in several direct and indirect manners. In this respect, the level of essential amino acids will be examined, the frequency of Tregs as well as the frequency of IL-17 producing cells. Furthermore, the effect of Arginase-specific T cells on the overall production of different cytokines including INF-γ, IL-6, TNF-α as well as IL-10 and TGF-β, will be examined. Another possible effect of Arginase-specific T cells could be mediated through the metabolites of arginin. Furthermore, the phenotype of the Arginase-specific T cells by FACS as well as analysing the cytokine profile of such T cells will be described. Furthermore, the expression of co-stimulatory molecules (FACS), direct or indirect killing of effector cells and APC (cytotox assays), will be addressed. The use of leukapheresis samples from cancer patients containing huge numbers of T cells will make it possible to perform experiments with a natural subset of Arginase-specific T cells directly isolated from donors.

Peptides

The sequences of the peptides used in these experiments are shown in full in Table A below (see the section entitled "Sequences"). Peptides are described in Table A by SEQ ID NO, by name, or by reference to the start and end positions of each peptide sequence within the full length sequence of Arginase 1. Each may be used interchangeably. For example, the peptide of SEQ ID NO: 34 may alternatively be referred to by the name Arg1-17 or may alternatively be referred to as Arg 161-190 (given a start position of 161 and end position of 190). The intended reference in each case will be clear from the context. The peptide of SEQ ID NO: 9 may additionally be referred to as ArgShort.

20-mer and 22-mer peptides were synthesized by PepScan (Netherlands) and dissolved in DMSO at 10 mM. 30-mer and 50-mer peptides were synthesized by Schafer-N ApS (Denmark) and dissolved in DMSO at 10 mM stock. Shorter peptides were synthesized by KJ Ross-Petersen ApS (Denmark) and dissolved in sterile water to a stock concentration of 2 mM. Purity of the synthesized peptides was >80%.

Example 1

Patients, Protocols and Methods
Patient Material:

The present project is based on analyses of blood and tumor lesions from melanoma, renal cell carcinoma and ovarian cancer patients. Collection of blood and tumor samples was conducted at Herlev Hospital. Blood samples were drawn a minimum of four weeks after termination of any kind of anti-cancer therapy. PBMC were isolated using Lymphoprep™ (Alere A S, cat. 1114547) separation, HLA-typed and frozen in FCS with 10% DMSO (Sigma-Aldrich, cat. D5879-100 ML). The immediate processing of the material was handled at the CCIT (Centre for Cancer Immunotherapy) in accordance with local ethical requirements. All patients only participate upon written informed consent, and that the ethical committee have approved the projects.

Enzyme-Linked Immunospot (ELISPOT):

Using the "ELISPOT" technique it is possible to screen for T-cell recognition of a high number of peptide antigens despite the availability of relatively few T-cells. The "ELISPOT" technique takes advantage of the fact that T-cells synthesize cytokines e.g. IFN-γ upon TCR engagement and subsequent signaling. The method may be used to analyze for secretion of any cytokine of choice—in our laboratory we routinely use IFN-γ, TNF-α, IL-10, Granzyme-B as well as perforin—ELISPOT analyses. Standardized quantitation is accomplished by the use of an ELISPOT reader (IMMUNOSPOT, CTLanalyzers LLC http://www.immunospot.com/).

Cytotoxicity Assay

Conventional $^{51}$Cr-release assays for CTL-mediated cytotoxicity were carried out as described elsewhere [3]. Target cells were T2-cells (ATCC), HLA-A$^{2+}$ melanoma cell lines (FM3 and FM93)

FACS:

Over the past years, new strong FACS techniques have been developed—in particular for studies of immune function and specificity. In this respect, peptide/HLA complexes are readily used for analyzing the frequency of peptide specific T-cells. Specific T-cells can be isolated and expanded in vitro. For Intracellular stainings, cells were stimulated with Arginase derived peptide and for surface markers we employed 4 µl NIR, 10 µl CD4 PerCP, 2 µl CD8 Pacific Blue, and 10 µl CD3 FITC and for intracellular staining we used 2 µl anti-TNF-a and anti-IFN-g antibodies conjugated with either PE-Cy7 or APC. Washing, permeabilization and staining procedures followed previously described methods [4]. Flow cytometry analysis was performed on a FACSCANTO II (BD Biosciences, San Jose Calif., USA)

Figure 1:
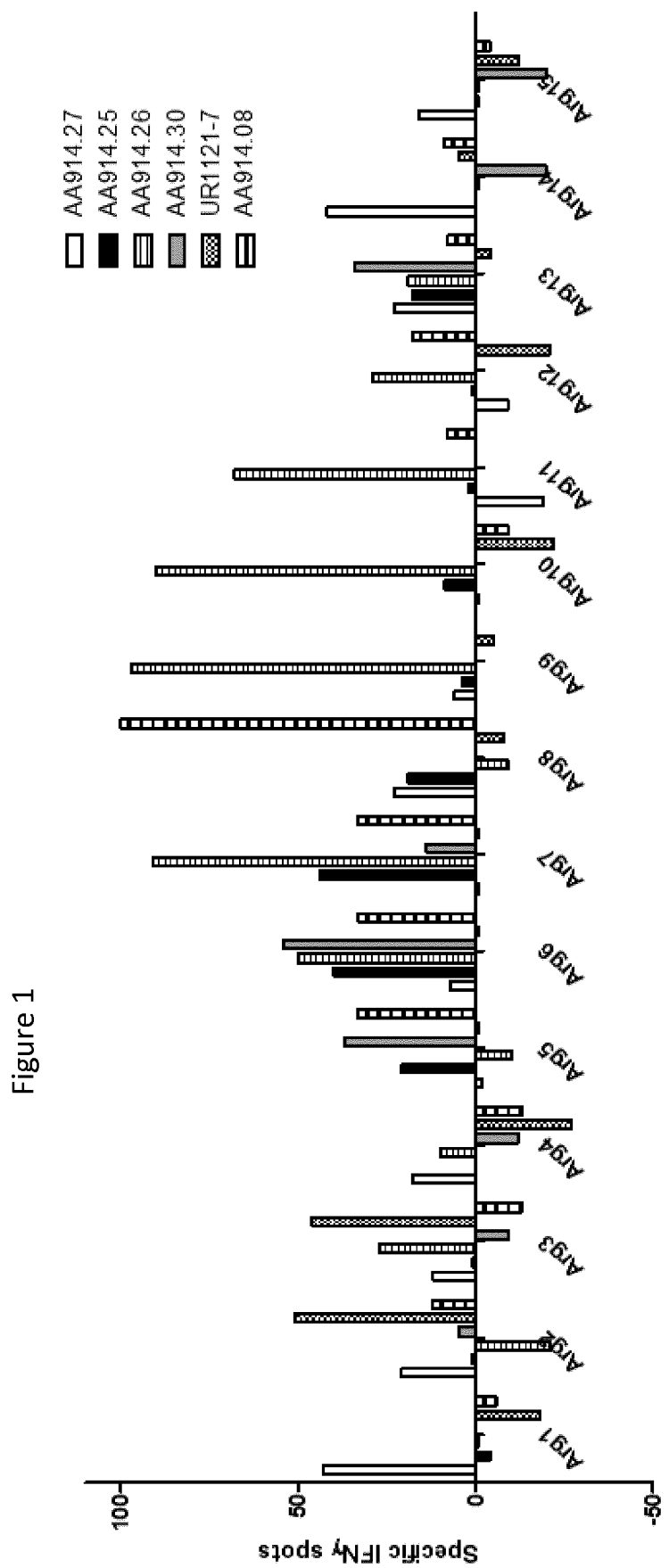
FIG. 1 shows T cell responses in samples from 6 cancer patients to the peptides consisting of each of the amino acids sequences of SEQ ID NOs: 2 to 16 (Arg1 to Arg15).
Figure 2:
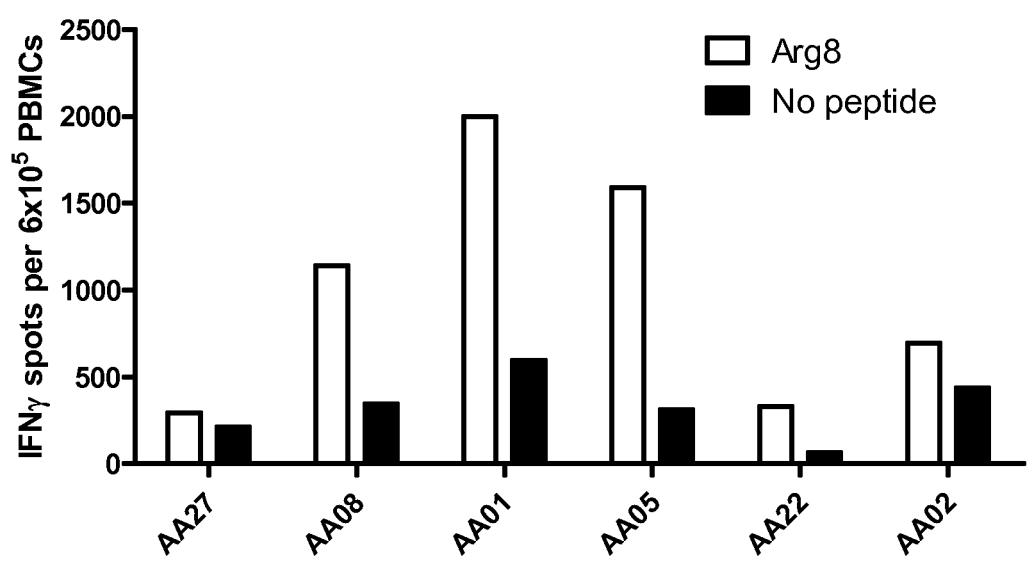
FIG. 2 shows T cell responses in samples from 6 cancer patients against the peptide consisting of each of the amino acid sequence of SEQ ID NO: 9 (Arg8).

Results:

16 peptides derived from Arginase 1 were designed. These peptides are referred to herein as Arg 1 to Arg 16 (SEQ ID NOs: 12 to 17). The sequences of these peptides are shown in full in Table A below (see the section entitled "Sequences"). 15 of the peptides (Arg1 to Arg15) were examined in ELISPOT. We scrutinized peripheral blood mononuclear cells (PBMC) from six melanoma patients for the presence of specific T-cell responses against Arg-derived peptide using the IFN-gamma ELISPOT secretion assay. Strong responses against Arg2 (SEQ ID NO 3), Arg3 (SEQ ID NO 4), Arg5 (SEQ ID NO 6), Arg 6 (SEQ ID NO 7), Arg7 (SEQ ID NO 8), Arg8 (SEQ ID NO 9), Arg9 (SEQ ID NO 10), Arg 10 (SEQ ID NO 11), Arg11 (SEQ ID NO 12), Arg14 (SEQ ID NO 15), Arg15 (SEQ ID NO 16) were detected. FIG. 1 exemplifies Arg-specific T cell responses. Especially Arg8 (SEQ ID NO 9) was examined in more detail. Patient PBMC hosting immune responses towards Arg8. Immune responses (specific cells/3×10e5 cells) from 6 cancer patients against Arginase-derived Arg 8 peptide as seen in FIG. 2. Very strong responses were frequently detected among patients PBMC.

Figure 3:
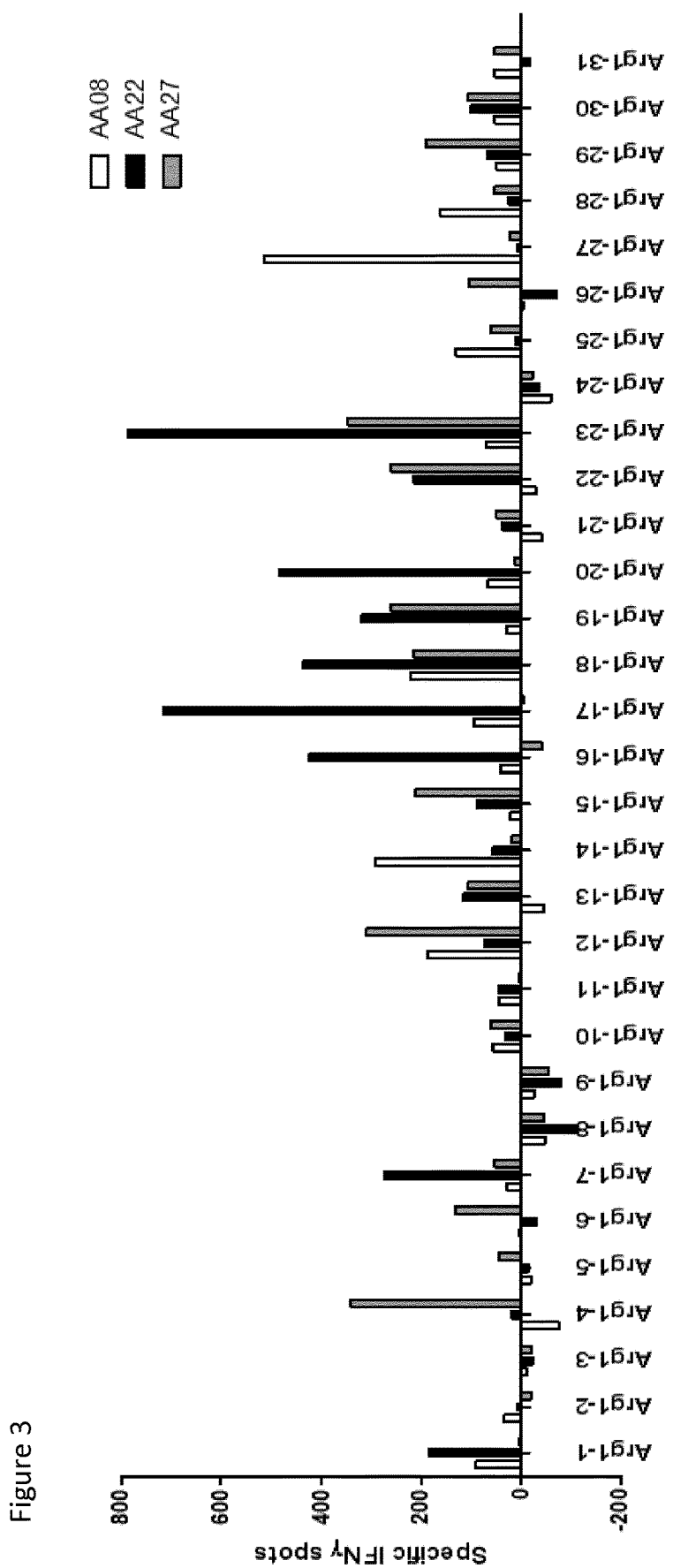
FIG. 3 shows T cell responses in samples from 3 cancer patients to the peptides of consisting of each of the amino acid sequences of SEQ ID NOs: 18 to 48 (Arg1-1 to Arg1-31).
Figure 4:
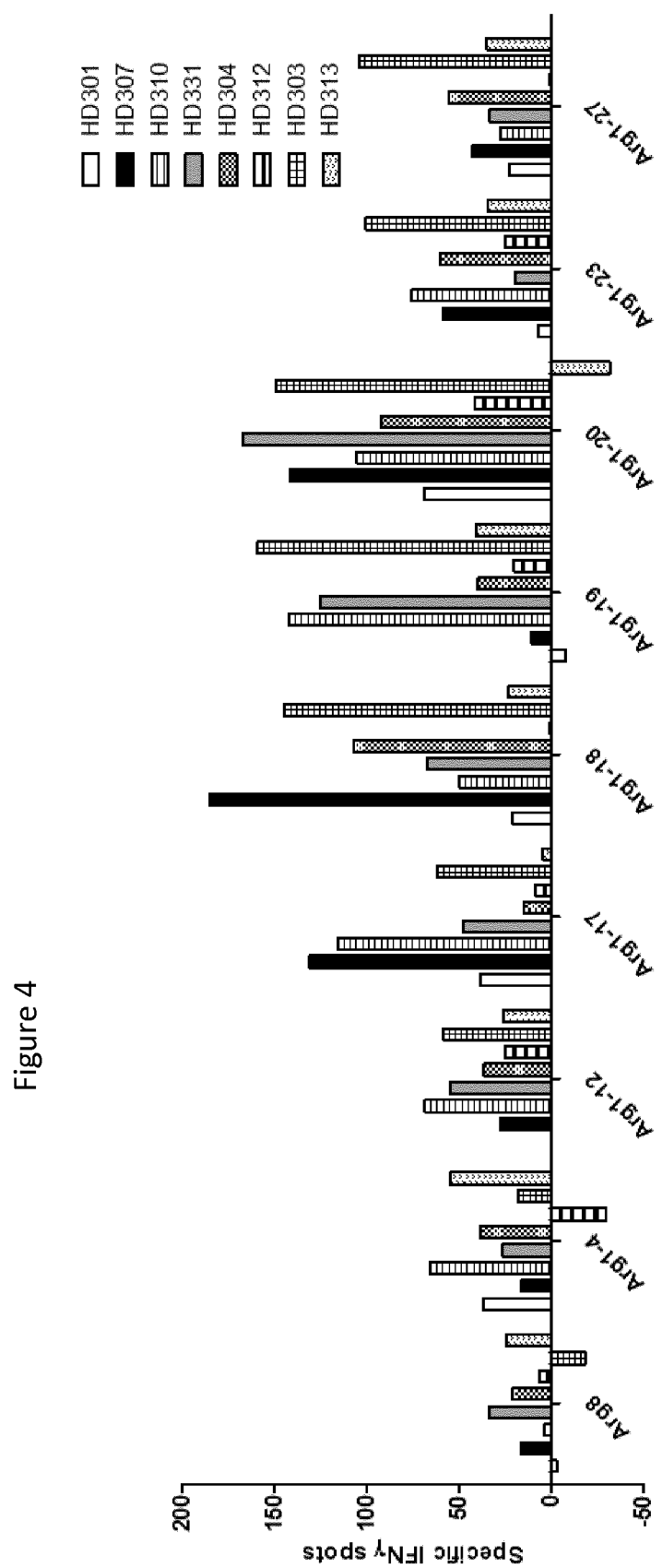
FIG. 4 shows T cell responses in samples from 8 healthy individuals against the peptides consisting of the amino acid sequence of each of SEQ ID NO: 9 (Arg8), SEQ ID NO: 21 (Arg1-4), SEQ ID NO: 29 (Arg1-12), SEQ ID NO: 34 (Arg1-17), SEQ ID NO: 35 (Arg1-18), SEQ ID NO: 36 (Arg1-19), SEQ ID NO: 37 (Arg1-20), SEQ ID NO: 40 (Arg1-23), SEQ ID NO: 44 (Arg1-17).

We next examined overlapping 20mer overlapping peptides spanning the entire Arginase sequence SEQ ID NO 1. Thus there are 30×20mer peptides and 1×22mer to span the entire length of the sequence. The sequences of these peptides are shown in full in Table A below (see the section entitled "Sequences") and correspond to SEQ ID NOs: 18 to 48. We used the above described peptides to examine immune responses in PMBC from three cancer patients seen in FIG. 3. Frequent immune responses were detected against several peptides especially the long peptides referred to as Arg1-23, Arg1-18, Arg1-27, Arg1-17, Arg1-19, Arg1-12, Arg1-20, Arg1-4, Arg1-1, Arg1-7, Arg1-14, Arg1-15, Arg1-6, Arg1-16, Arg1-22, Arg1-29. In addition, we show responses in PBMC from healthy individuals against these long peptides (FIG. 4).

Figure 5:
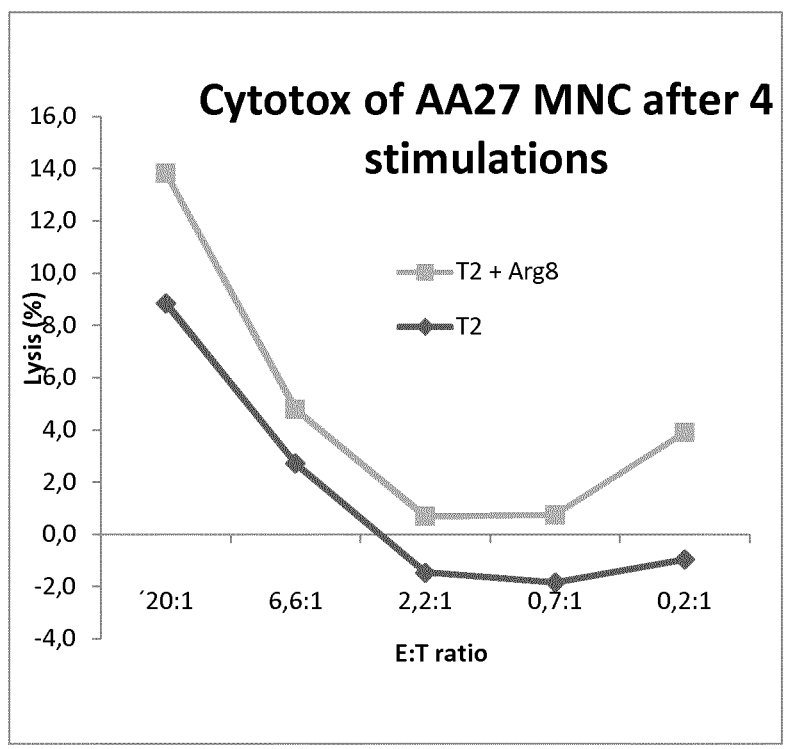
FIG. 5 shows CD8 positive culture can kill target cells loaded with the peptide consisting of each of the amino acid sequence of SEQ ID NO: 9 (Arg8).
Figure 6:
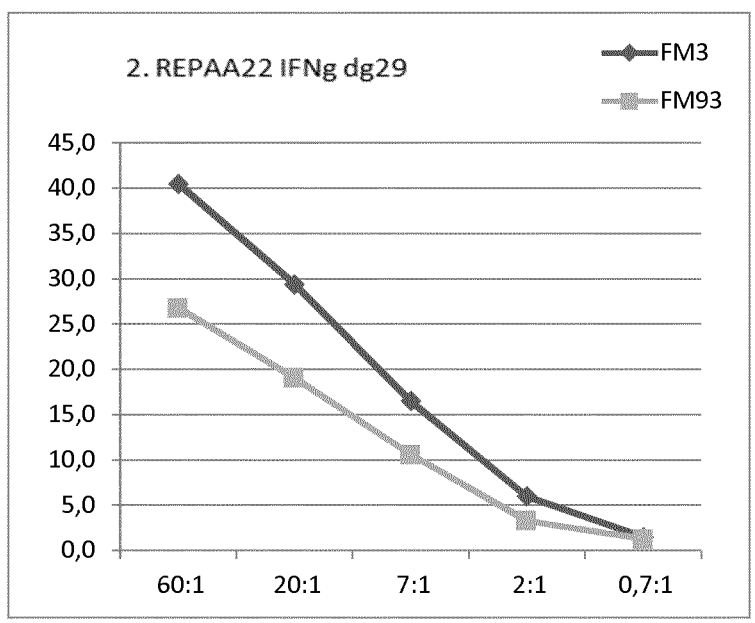
FIG. 6 shows killing of Arginase positive cancer (melanoma) cell lines FM3 and FM93 by Arginase specific T cells.

CD8 positive culture can kill target cells loaded with Arg8 on the surface as examined by standard chromium release assay as seen in FIG. 5. Killing of Arginase positive cancer (melanoma) cell lines FM3 and FM93 by Arginase specific T cells was also demonstrated using standard chromium release assays as seen in FIG. 6. In this experiment Arginase specific T cells were incubated 4 h with either Cr-labeled melanoma cell lines FM3 or FM93 at different effector:target ratios. Both cell lines express intracellular Arginase.

Figure 7:
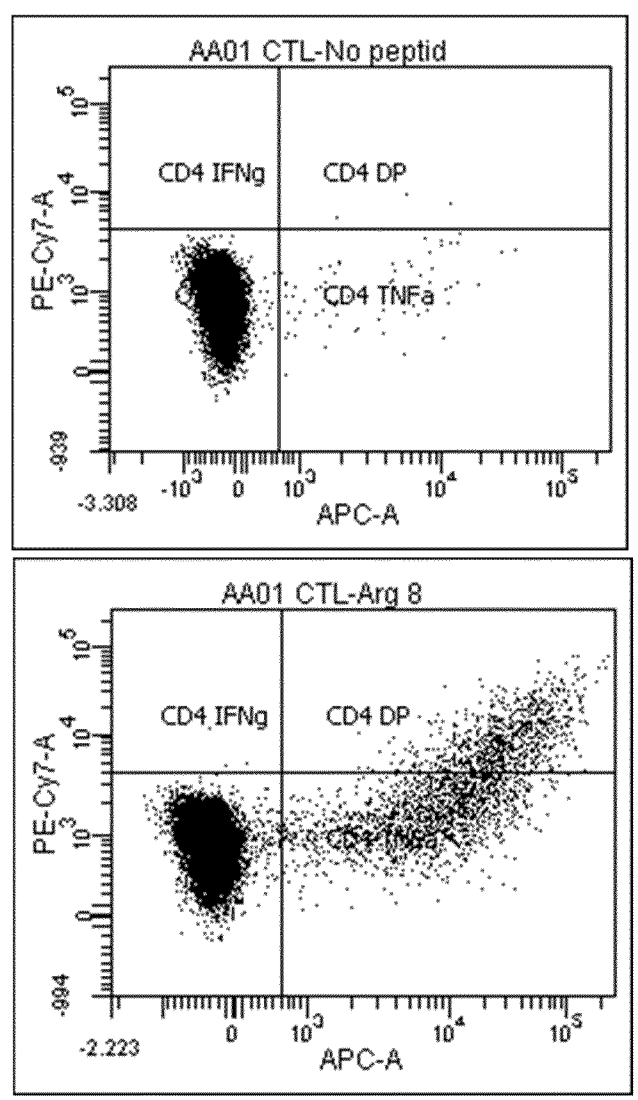
FIG. 7 shows flow cytometric analysis of CD4 Tcells from a cancer patient, assessed by intracellular staining for IFN-g (PE-Cy7A) and TNF-alpha (APC-A) following culture either without (top panel) or with (bottom panel) stimulation with the peptide consisting of each of the amino acid sequence of SEQ ID NO: 9 (Arg8). Similar results are shown in FIG. 8.
Figure 8:
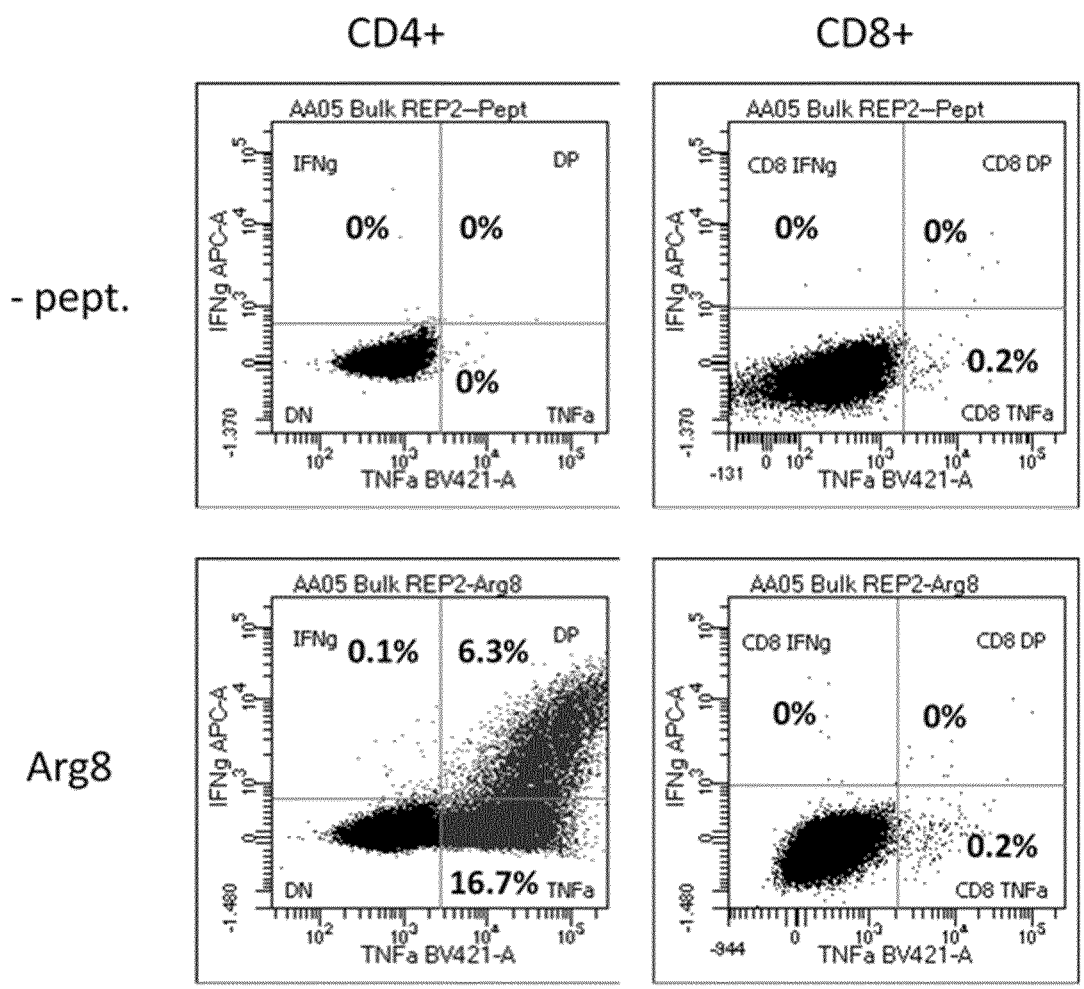

Next we examined if CD4 CD4 T-cells can recognize arginase after in vitro stimulation. Hence, we chose to analyze PBMC from a patient with a response against Arg8 using intracellular cytokine staining. Although this method is less sensitive than ELISPOT, it allows to elucidate which immune cells secrete the cytokine identified in ELISPOT. Hence, we stimulated CD4 T cells from a cancer patients 5 times with Arg8 peptide. Next, we performed Intracellular staining against INF (PE-Cy7A) and TNF-alfa (APC-A) of the T-cell culture after 5 stimulations in vitro with Arg8 peptide. The culture is either stimulated with or without Arg8 peptide as seen in FIG. 7. Similar results are seen in FIG. 8.

In conclusion: Both CD8 and CD4 T cells can recognize Arginase derived peptides on the surface of target cells. The region spanning positions 161 to 190 of Arginase1 appears to be particularly immunogenic. This region may be referred to herein as a hotspot.

Example 2

Materials and Methods
Additional Peptide Stimulation and ELISPOT Assay

PBMCs from healthy donors or cancer patients were stimulated with 80 µg of arginase-derived peptides and 120 U/ml IL-2 (Peprotech, London, UK, cat. 200-02) for a week. 4-6×10⁵ PBMCs were then placed in the bottom of ELISPOT plate (nitrocellulose bottomed 96-well plates by MultiScreen MAIP N45; Millipore, cat. MSIPN4W50) pre-coated with IFN-γ capture Ab (Mabtech, cat. 3420-3-1000) and 1-10 µg of arginase derived peptides were added. PBMCs from each patient and donors were set up in duplicates or triplicates for peptide and control stimulations. Cells were incubated in ELISPOT plates in the presence of an antigen for 14-16 hours after which they are washed off and secondary biotinylated Ab (Mabtech, cat. 3420-6-1000) was added. After 2 h incubation unbound secondary antibody was washed off and streptavidin conjugated alkaline phosphatase (AP) (Mabtech, cat. 3310-10) was added for 1 h. Next, unbound conjugated enzyme is washed off and the assay is developed by adding BCIP/NBT substrate (Mabtech, cat. 3650-10). Developed ELISPOT plates were analysed on CTL ImmunoSpot S6 Ultimate-V analyzer using Immunospot software v5.1. Responses were calculated as the difference between average numbers of spots in wells stimulated with Arginase-1 peptides and control wells.

HLA-Blocking

For blocking of HLA Class I and II, PBMCs were pre-incubated with 2 µg/ml of the blocking antibodies: anti-human HLA-DR, DP, DQ antibody CloneTü39 (Biolegend, cat. 361702) or anti-human HLA-ABC antibody Clone w6/32 (Dako, Agilent) for 20 min at RT before the addition of the peptide.

Establishment of Arginase-Specific T-Cell Cultures

Arginase-specific T cell culture were established by stimulation of cancer patient PBMC with irradiated ArgShort (SEQ ID NO 9) peptide-loaded autologous DC or PBMCs. The following day IL-7 and IL-12 (PeproTech, London, UK, cat. 200-07-10 and 200-12) were added. Stimulation of the cultures were carried out every 8 days with ArgShort peptide loaded irradiated autologous DC followed by ArgShort peptide-loaded irradiated autologous PBMC. The day after peptide stimulation IL-2 (PeproTech, London, UK, cat. 200-12) was added. After 5 stimulations arginase-specific T cells were enriched using TNF-α cell enrichment kit (MiltenyiBiotec, cat. 130-091-269).

Generation of Dendritic Cells

DCs were generated from PBMC by adherence on culture dishes at 37° C. for 1-2 hr. in RPMI-1640. Adherent monocytes were cultured in RPMI-1640 supplemented with 10% FCS in the presence of IL-4 (250 U/ml) and GM-CSF (1000 U/ml) (Peprotech, London, UK, cat. 200-04 and 300-03-100) for 6 days. DCs were matured by addition of IL-β (1000 U/ml), IL-6 (1000 U/ml) TNF-α (1000 U/ml) (Peprotech, London, UK, cat. 200-01B, 200-06 and 300-01A) and PGE2 (1 ug/ml) (Sigma Aldrich, cat. P6532).

B Cell Isolation

PBMCs from cancer patients were thawed and rested overnight. B cells were isolated from patient PBMCs using Pan B Cell Isolation Kit (Miltenyi Biotec Inc., cat. 130-101-638) according to manufacturer's instructions.

Production of In Vitro-Transcribed mRNA

The cDNA encoding Arginase (accession nr. NM_000045) was synthesized and cloned into either pSP73-SphA64 (kindly provided by Dr. E. Gilboa, Duke University Medical Center, Durham, N.C.) using 5'XhoI/3'PacI restriction sites (Geneart/Life Technologies) or into the HLA class II targeting plasmid pGEM-sig-DC.LAMP (kindly by provided by Dr. K. Thielemans, Medical School of the Vrije Universiteit Brussel) using 5'BamHI/3'BamHI restriction sites. Both plasmids were linearized with SpeI before serving as DNA template for in vitro transcription.

Electroporation

For mRNA experiments, dendritic cells and B cells were transfected with Arginase mRNA or control mRNA encoding GFP or nerve growth factor receptor (NGFR) using electroporation parameters as previously described. Briefly, cells were washed twice, suspended in Opti-MEM medium (Invitrogen, cat. 11058021) and adjusted to a final cell density of 4-7×10⁶ cells/ml. The cell suspension (200-300 ul) was pre-incubated on ice for 5 min and 5-10 µg of mRNA was added. Cell suspension was then transferred into a 4-mm gap electroporation cuvette and electroporated. Electroporated cells were further incubated in humidified atmosphere with 5% CO2 and used for experimental analysis as specified. Electroporation efficiency was determined 24 hours later by FACS analysis of the GFP or NGFR transfected cells.

Flow Cytometric Analysis

Flow cytometry analysis was performed on a FACSCanto™ II (BD Biosciences, San Jose Calif., USA). Intracellular staining of cell cultures was performed after the cells were stimulated with 20-mere peptides for 5 hours or 30-mere peptides for 8 h (BD GolgiPlug™ cat. 555029, was added after the first hour). The cells were then stained for surface markers, then washed and permeabilized by using Fixation/Permeabilization and Permeabilization Buffer (eBioscience, cat. 00-5123-43), according to manufacturer's instructions. Antibodies used: IFNγ-APC (cat. 341117), TNFα-BV421 (cat. 562783), CD4-FITC (cat. 347413), CD8-PerCP (cat. 345774) (all from BD Biosciences). Dead cells were stained using FVS510 (564406, BD Biosciences) according to manufacturer's instructions.

Results

Spontaneous Immune Responses Against Arginase-1

Figure 9:
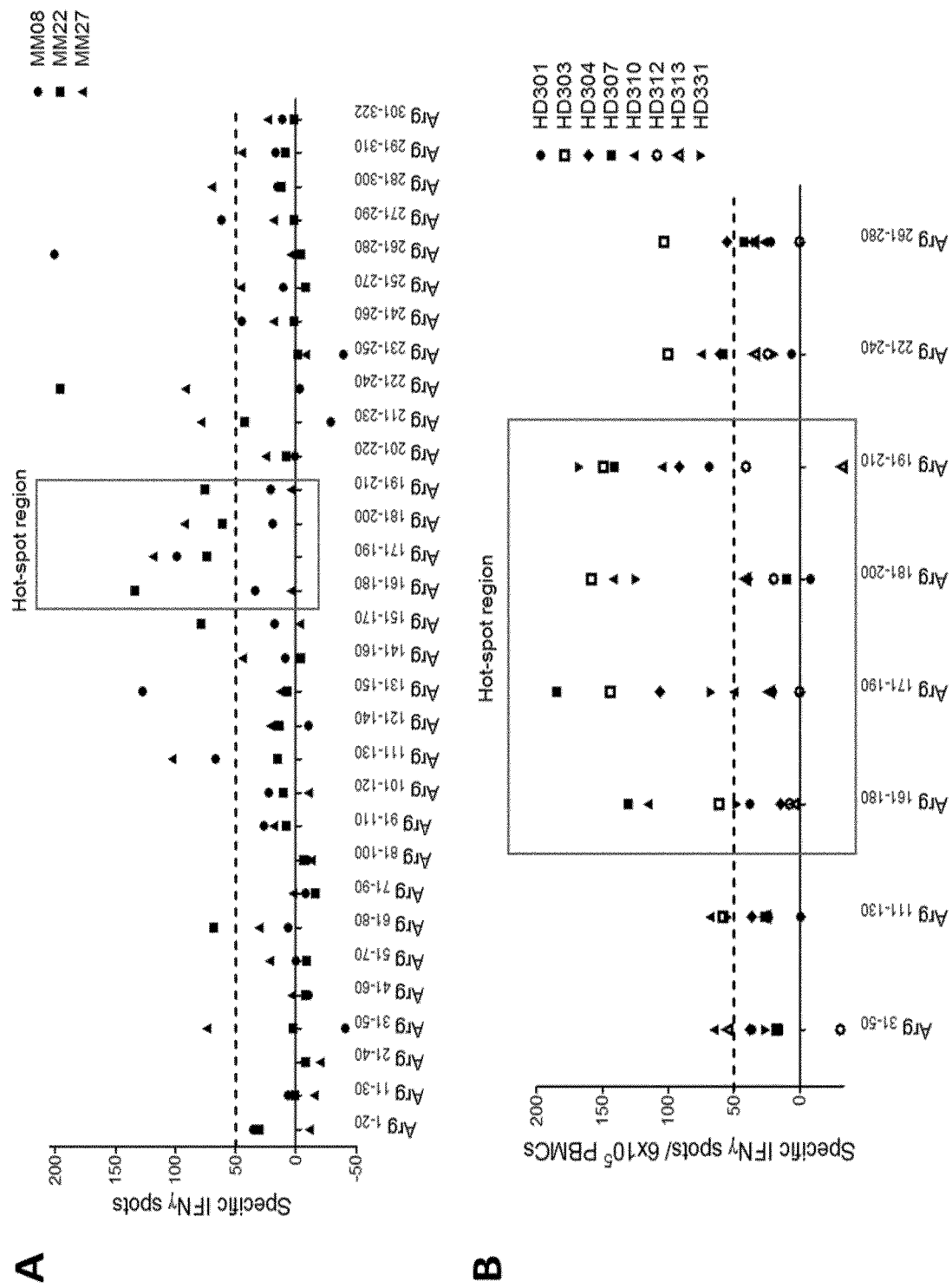
FIG. 9 shows that multiple arginase-1 peptides are recognized by PBMCs from 3 melanoma patients (9A) and 8 healthy donors (9B) when assessed by IFNγ ELISPOT. Peptides are described by reference to the start and end positions of their sequences within the sequence of human Arginase 1. Spot counts are given as a difference between averages of the wells stimulated with the peptide and control wells. Peptide and control stimulations were performed in duplicates or triplicates.

We divided the entire arginase-1 protein sequence into overlapping 20-amino-acid-long peptides, generating a library of 31 peptides covering the whole sequence (SEQ ID NOs 18-48)). Each peptide in the library overlapped with the first 10 amino acids of the following peptide. Using this arginase peptide library and the IFNγ ELISPOT assay, we next screened PBMCs from melanoma patients and healthy donors for spontaneous responses (FIGS. 9A and 9B). The PBMCs were stimulated for one week with a pool of 3-4 adjacent 20-mer arginase library peptides and low-dose IL-2 (120 U/mL). They were then set up for an IFNγ ELISPOT assay to screen for responses against each 20-mer peptide separately. The following eight peptides showed the highest and most abundant responses in cancer patient PBMCs (peptides labelled by reference to start and end position): Arg(31-50), Arg(111-130), Arg(161-180), Arg(171-190), Arg(181-200), Arg(191-210), Arg(221-240), and Arg(261-280). Among these overlapping peptides, Arg(161-180), Arg(171-190), Arg(181-200), and Arg(191-210) spanned a 50-amino-acid-long region that was deemed a hot-spot region since nearly all patients harbored a response against one or more of these peptides (FIG. 9A). The selected eight peptides were further used to screen for spontaneous immune responses against arginase-1 in PBMCs from eight healthy donors using IFNγ ELISPOT. As in the PBMCs from cancer patients, the PBMCs from healthy donors showed the highest IFNγ responses against the four arginase peptides in the hot-spot region (FIG. 9B).

Arginase-1 Responses in Melanoma TILs

Figure 10:
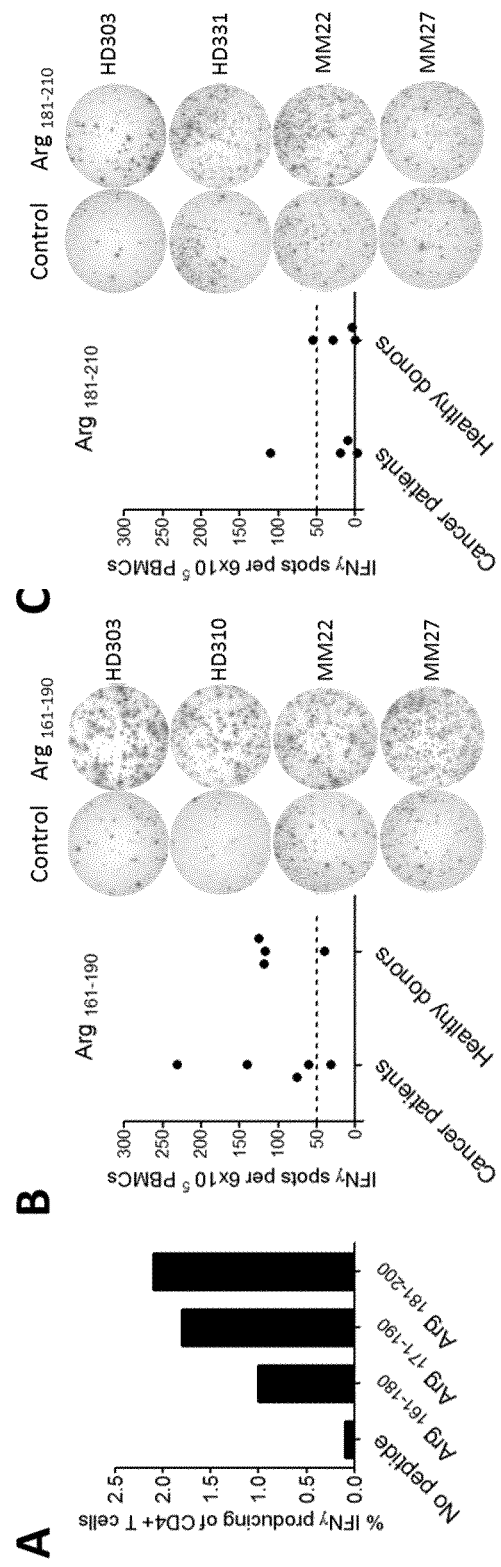
FIG. 10 shows that the region corresponding to positions 161 to 210 of SEQ ID NO: 1 is widely recognized by cancer patient and healthy donor PBMCs A—shows the proportion of CD4+ T cells in tumour infiltrating lymphocytes (TILs) from melanoma patient which release IFNγ in response to the peptides consisting of the amino acid sequences of each of SEQ ID NO: 34 (Arg161-180), SEQ ID NO: 35 (Arg171-190) and SEQ ID NO: 36 (Arg181-200). Peptide names refer to the start and end positions of their sequences within the sequence of human Arginase 1

To investigate the potential presence of arginase-specific T cells among tumor-infiltrating lymphocytes in cancer, we screened TILs from eight melanoma patients for responses against arginase-1 derived peptides. To this end, we performed intracellular staining for IFNγ and TNFα release in response to peptide stimulation. TILs were thawed and rested overnight without IL-2, and then stimulated for 5 h with three hot-spot immunogenic region 20-mer peptides (peptides labelled by reference to start and end position): Arg(161-180), Arg(171-190), Arg(181-200). In one of the TIL cultures, IFNγ was released from CD4+ T cells in response to stimulation with all three arginase peptides (FIG. 10A), suggesting that the arginase-1 hot-spot region likely contained a number of CD4+ T-cell epitopes. The percentage of IFNγ-producing cells was higher for Arg(171-190) and Arg(181-200) compared to Arg(161-180), and the response against Arg(181-200) was almost twice that against Arg (161-180). No IFNγ or TNFα release was observed from CD8+ T cells.

Arginase-1 Hot-Spot Region is Recognized by CD4+ and CD8+ T Cells

Since we most frequently observed responses against arginase-1 peptides from the hot-spot region, we next analyzed whether longer peptides covering the same sequence could be used instead of four 20-mers. A 50-mer peptide covering the entire hot-spot region elicited lower responses compared to the 20-mer peptides (data not shown). We then divided the arginase-1 hot-spot region into two 30-mer peptides that overlapped by 10 amino acids (peptides labelled by reference to start and end position): Arg(161-190) and Arg(181-210). These 30-mer peptides were used to check for responses in selected PBMCs from cancer patients and healthy donors, which had previously shown responses against the 20-mer hot-spot peptides. The PBMCs were stimulated for one week with either Arg(161-190) or Arg (181-210) in the presence of IL-2, and were then used in IFNγ ELISPOT. PBMCs from both cancer patients and healthy donors showed high responses against Arg(161-190) (FIG. 10B), comparable to the responses against 20-mer peptides. Some PBMCs also showed responses against the 30-mer Arg(181-210) peptide (FIG. 10C); however, these responses were lower than those against the overlapping 20-mer peptides covering the same protein region (FIG. 9B).

To investigate which types of T cells reacted to the peptide epitopes in the hot-spot region, we performed intracellular staining for IFNγ and TNFα release in PBMCs from two healthy donors and one cancer patient, which had shown responses against the Arg(161-190) peptide in IFNγ ELISPOT. We detected TNFα release from CD4+ T cells after an 8-hour incubation with Arg(161-190) (FIG. 11A). We also detected a minor response from CD8+ T cells in some samples (data not shown), suggesting the presence of HLA Class I and II epitopes in the arginase-1 hot-spot region. Blocking HLA Class I or Class II expression partially blocked the IFNγ release in response to Arg(161-190) peptide stimulation, further demonstrating that Arg(161-190) contained CD4+ and CD8+ T cell epitopes (FIG. 11B).

We generated an arginase-specific CD4+ T-cell culture by repeated stimulation of PBMCs from a melanoma patient with DCs and PBMCs that were loaded with a minimal arginase peptide (ArgShort) located in the hot-spot region. The T-cell culture specific against the minimal arginase epitope also recognized the 30-mer Arg(161-190) peptide in IFNγ ELISPOT (FIG. 11C, left) and intracellular staining (FIG. 11C, right). However, the 50-mer peptide covering the entire hot-spot region was not recognized. After 8 hours of Arg(161-190) peptide stimulation, intracellular staining revealed TNFα release from CD4+ T cells.

T-Cell Recognition Dependent on Arginase-1 Expression

To assess the ability of arginase-specific CD4+ T cells to recognize and react against immune cells producing arginase-1, we transfected autologous dendritic cells and B cells with mRNA encoding arginase-1 protein. Autologous DCs were transfected with two different constructs encoding arginase-1 mRNA. One of these constructs contained the arginase-1 sequence fused to the DC-LAMP signal sequence, which targets a protein towards the lysosomal compartment and thus directs that protein towards Class II presentation. Arginase-specific CD4+ T-cell cultures from two different melanoma patients were rested without IL-2 for 24 h, and then set up for IFNγ ELISPOT with electroporated autologous DCs or B cells. We observed higher reactivity against DCs and B cells that were transfected with arginase-1 mRNA compared to Mock control (FIG. 12A-D). The responses were even higher against the DCs transfected with arginase-DC-LAMP compared to both Mock control and arginase-1 mRNA (FIG. 12E). After 24 h, we checked the electroporation efficiency of DCs via FACS analysis of GFP/NGFR-expressing cells, finding >90% transfection efficiency.

CONCLUSION

These experiments confirm that the region spanning positions 161 to 190 of Arginase1 is particularly immunogenic in both cancer patients and healthy donors, giving rise to both CD4 and CD8 positive T cell responses. The region may contain multiple HLA Class I and Class II restricted. Peptides derived from this region may be particularly effective in a vaccine against Arginase1. Such a vaccine would be expected to have treatment benefits in cancer.

Example 3—In Vivo Experiments

Design of Peptides for In Vivo Experiments

In order to design peptides suitable for use in vaccination experiments in mice, the sequence of murine Arginase1 (SEQ ID NO: 59) was compared to the human Arginase1 sequence of SEQ ID NO: 1. See alignment shown in FIG. 13, which demonstrates that the sequences have a high level of similarity. The level of similarity is particularly high in the hotspot region of human Arginase1 described in the above examples, i.e. the region corresponding to positions 161-210 of SEQ ID NO: 1—this 50 amino acid region is shown in bold for both sequences in FIG. 13. An alignment of this region and the corresponding region in murine Arginase 1 is also shown below:

hArg1:
(SEQ ID NO: 52)
GFSWVTPCISAKDIVYIGLRDVDPGEHYILKTLGIKYFSMTEVDRLGIGK mArg1:
(SEQ ID NO: 57)
GFSWVTPCISAKDIVYIGLRDVDPGEHYIIKTLGIKYFSMTEVDKLGIGK

Only 2 residues of the 50 differ, shown as bold and underlined. A leucine in the human sequence is substituted for the highly similar aliphatic amino acid isoleucine in the mouse, and an arginine in the human sequence is substituted for the similarly basic lysine in the mouse. Both changes are conservative. Accordingly the hotspot region is highly conserved between humans and mice.

Given the above similarity, it was determined that relatively few changes would be required to create murine analogues of the human peptides tested in the previous examples. The peptides used were therefore as follows:

(SEQ ID NO: 34)
GFSWVTPCISAKDIVYIGLR

ARG17 is the sequence of positions 161-180 of human Arginase 1 (SEQ ID NO: 1). The corresponding region in murine Arginase 1 is identical. (Also referred to interchangeably as ARG1-17 and ARG(161-180) in previous Examples).

(SEQ ID NO: 36)
DVDPGEHYILKTLGIKYFSM

ARG1-19 is the sequence of positions 181-200 human Arginase 1 (SEQ ID NO: 1). The corresponding region in murine Arginase1 differs in a single position (the bold underlined L is replaced with I in the murine sequence). (Also referred to interchangeably as ARG(181-200) in previous Examples).

(SEQ ID NO: 53)
KDIVYIGL mARG1 is the sequence of positions 172-179 of human Arginase 1 (SEQ ID NO: 1). The corresponding region in murine Arginase 1 is identical.

(SEQ ID NO: 54)
LGIKYFSM mARG2 is the sequence of positions 193-200 of human Arginase 1 (SEQ ID NO: 1). The corresponding region in murine Arginase 1 is identical.

(SEQ ID NO: 56)
KTLGIKYFSMTEVDKLGIGK mARG20 is the sequence of positions 191-210 of murine Arginase 1 (SEQ ID NO: 59). The corresponding region in human Arginase1 is SEQ ID NO: 37 and differs in a single position (the bold underlined K is replaced with R in the human sequence).

Peptide Vaccination of C57BL/6 and Balb/c Mice

Animals were vaccinated subcutaneously with 100 g peptide in DMSO/$H_2O$ in a 1:1 emulsion with incomplete Freund's adjuvant (IFA) or montanide. IFA+DMSO/$H_2O$ served as a control vaccine. Vaccinations were carried out on day0 and day7. For subsequent analysis of the immune response to specific peptides, mice were sacrificed on day 14 and spleen and draining lymph nodes (dLNs) were harvested.

ELISPOT Analysis of Peptide-Specific Response

Murine immune cells were subjected to ELISPOT analysis. Single cell suspension was prepared from spleen or dLNs by passage through a cell strainer. After lysis of red blood cells, 0.9×10E6 cells/well were seeded into ELISPOT plates coated with anti-IFNgamma antibody. Peptide of interest was added to designated wells and cells were incubated o/n with peptide. The next day, cells were removed, plates washed and incubated with biotinylated detection antibody. Finally, after addition of Streptavidin-ALP and substrate visible spots appear. Each spot corresponds to an individual IFNgamma producing cell. Plates were analysed in an Immunospot analyser and plotted as spots/0.9×10E6 cells minus background (i.e. minus number of spots in corresponding unstimulated (no peptide) wells).

Tumor Vaccination of Male Balb/c Mice, Age 9-10 Weeks, 4 Animals Per Group

Each animal was inoculated subcutaneously into the left flank with 0.5×10E6 syngeneic CT26.WT colon cancer cells in 100 µl PBS. On day6 after inoculation when tumors were palpable, animals received the first vaccination of peptide or control vaccine (as described above for peptide vaccination). On day 13, animals received the second vaccination. Tumor growth was monitored and tumors were measured 3× per week. Tumor volume was calculated at V $[mm^3]=1 \times w^2/2$ (where l is the longest diameter and w perpendicular to l).

Results

ARG17, ARG1-19 and mARG20 were all found to be immunogenic in both C57BL/6 and Balb/c mice. Peptide specific responses were detected in both C57BL/6 and Balb/c mice vaccinated with each of ARG17, ARG1-19 and mARG20 (see FIGS. 14-15). Of the shorter peptides, mARG1 was immunogenic in C57BL/6 mice and mARG2 was not immunogenic in either strain (data not shown).

In the tumour inoculation experiments, vaccination with each of ARG17, ARG1-19 and mARG20 was found to inhibit tumor growth relative to vaccination with control peptide. The effect was most noticeable with ARG1-19 and mARG20, although a treatment benefit was apparent for all three tested peptides. This confirms the potential of the peptides of the invention (and of vaccination against Arginase 1 in general) as treatments for cancer.

The lower responses to ARG17 may reflect a lack of stability of that peptide, e.g. due to the presence of a cysteine residue. Replacement of that amino acid by conservative substitution could solve this problem without altering other properties of the sequence of Arg1 defined by positions 161-180. However, these results also suggest that the sequence of Arg1 defined by positions 181-200 and particularly 191-210 may be preferred in that they are easy to manufacture, stable and appear to generate best responses in mice.

REFERENCES

[1] Bronte V, Zanovello P (2005) Regulation of immune responses by L-arginine metabolism. Nat Rev Immunol 5:641-54.
[2] Mussai F, De S C, Abu-Dayyeh I, Booth S, Quek L, McEwen-Smith R M, et al. (2013) Acute myeloid leukemia creates an arginase-dependent immunosuppressive microenvironment. Blood 122:749-58.
[3] Andersen M H, Bonfill J E, Neisig A, Arsequell G, Sondergaard I, Valencia G, et al. (1999) Phosphorylated Peptides Can Be Transported by TAP Molecules, Presented by Class I MHC Molecules, and Recognized by Phosphopeptide-Specific CTL. J Immunol 163:3812-8.
[4] Ahmad S M, Martinenaite E, Hansen M, Junker N, Borch T H, Met O, et al. PD-L1 peptide co-stimulation increases immunogenicity of a dendritic cell-based cancer vaccine. in press ed. 2016.

```
                              SEQUENCES
Full length human Arginase 1 (NP_000036.2) (SEQ ID NO: 1)
MSAKSRTIGI IGAPFSKGQP RGGVEEGPTV LRKAGLLEKL KEQECDVKDY GDLPFADIPN
DSPFQIVKNP RSVGKASEQL AGKVAEVKKN GRISLVLGGD HSLAIGSISG HARVHPDLGV
IWVDAHTDIN TPLTTTSGNL HGQPVSFLLK ELKGKIPDVP GFSWVTPCIS AKDIVYIGLR
DVDPGEHYIL KTLGIKYFSM TEVDRLGIGK VMEETLSYLL GRKKRPIHLS FDVDGLDPSF
TPATGTPVVG GLTYREGLYI TEEIYKTGLL SGLDIMEVNP SLGKTPEEVT RTVNTAVAIT
LACFGLAREG NHKPIDYLNP PK
Region identified as a hotspot for immunogenicity shown bold and underlined NOTE: the above sequence is isoform2 of human Arginase 1, which has the most
widespread distribution of expression. An alternative, longer isoform1 is expressed
predominantly in the liver. The sequence for this form is provide as NP_001231367.1.
It includes an additional 8 amino acid sequence (VTQNFLIL, SEQ ID NO: 62) inserted
between positions corresponding to positions 43 and 44 of isoform 2 as shown in SEQ
ID NO: 1. Any polypeptide of the invention which spans those positions of isoform2
may optionally include the insertion of the said additional 8 amino acids of isoform1.

Full length murine Arginase 1 (NP_031508.1) (SEQ ID NO: 59)
MSSKPKSLEI IGAPFSKGQP RGGVEKGPAA LRKAGLLEKL KETEYDVRDH GDLAFVDVPN
DSSFQIVKNP RSVGKANEEL AGVVAEVQKN GRVSVVLGGD HSLAVGSISG HARVHPDLCV
IWVDAHTDIN TPLTTSSGNL HGQPVSFLLK ELKGKFPDVP GFSWVTPCIS AKDIVYIGLR
DVDPGEHYII KTLGIKYFSM TEVDKLGIGK VMEETFSYLL GRKKRPIHLS FDVDGLDPAF
TPATGTPVLG GLSYREGLYI TEEIYKTGLL SGLDIMEVNP TLGKTAEEVK STVNTAVALT
LACFGTQREG NHKPGTDYLK PPK
Region identified as a hotspot for immunogenicity shown bold and underlined Full length human Arginase 2 (NP_001163.1) (SEQ ID NO: 60)
MSLRGSLSRL LQTRVHSILK KSVHSVAVIG APFSQGQKRK GVEHGPAAIR EAGLMKRLSS
LGCHLKDFGD LSFTPVPKDD LYNNLIVNPR SVGLANQELA EVVSRAVSDG YSCVTLGGDH
SLAIGTISGH ARHCPDLCVV WVDAHADINT PLTTSSGNLH GQPVSFLLRE LQDKVPQLPG
FSWIKPCISS ASIVYIGLRD VDPPEHFILK NYDIQYFSMR DIDRLGIQKV MERTFDLLIG
KRQRPIHLSF DIDAFDPTLA PATGTPVVGG LTYREGMYIA EEIHNTGLLS ALDLVEVNPQ
LATSEEEAKT TANLAVDVIA SSFGQTREGG HIVYDQLPTP SSPDESENQA RVRI
Region identified as a hotspot for immunogenicity shown bold and underlined
```

TABLE A

| SEQ ID NO | Sequence | Name | Start pos | End pos |
|---|---|---|---|---|
| 2 | QLAGKVAEV | Arg1 | 79 | 87 |
| 3 | LVLGGDHSL | Arg2 | 95 | 103 |
| 4 | LLKELKGKI | Arg3 | 148 | 156 |
| 5 | ELKGKIPDV | Arg4 | 151 | 159 |
| 6 | VMEETLSYL | Arg5 | 211 | 219 |
| 7 | HLSFDVDGL | Arg6 | 228 | 236 |
| 8 | SLGKTPEEV | Arg7 | 281 | 289 |

TABLE A-continued

| SEQ ID NO | Sequence | Name | Start pos | End pos |
|---|---|---|---|---|
| 9 | IVYIGLRDV | Arg8 | 174 | 182 |
| 10 | GLLSGLDIM | Arg9 | 268 | 276 |
| 11 | DIMEVNPSL | Arg10 | 274 | 282 |
| 12 | LLSGLDIMEV | Arg11 | 269 | 278 |
| 13 | NLHGQPVSFL | Arg12 | 139 | 148 |
| 14 | SLVLGGDHSL | Arg13 | 94 | 103 |
| 15 | YLLGRKKRPI | Arg14 | 218 | 227 |
| 16 | VLGGDHSLAI | Arg15 | 96 | 105 |
| 17 | FLLKELKGKI | Arg16 | 147 | 156 |
| 18 | MSAKSRTIGIIGAPFSKGQP | Arg1-1 | 1 | 20 |
| 19 | IGAPFSKGQPRGGVEEGPTV | Arg1-2 | 11 | 30 |
| 20 | RGGVEEGPTVLRKAGLLEKL | Arg1-3 | 21 | 40 |
| 21 | LRKAGLLEKLKEQECDVKDY | Arg1-4 | 31 | 50 |
| 22 | KEQECDVKDYGDLPFADIPN | Arg1-5 | 41 | 60 |
| 23 | GDLPFADIPNDSPFQIVKNP | Arg1-6 | 51 | 70 |
| 24 | DSPFQIVKNPRSVGKASEQL | Arg1-7 | 61 | 80 |
| 25 | RSVGKASEQLAGKVAEVKKN | Arg1-8 | 71 | 90 |
| 26 | AGKVAEVKKNGRISLVLGGD | Arg1-9 | 81 | 100 |
| 27 | GRISLVLGGDHSLAIGSISG | Arg1-10 | 91 | 110 |
| 28 | HSLAIGSISGHARVHPDLGV | Arg1-11 | 101 | 120 |
| 29 | HARVHPDLGVIWVDAHTDIN | Arg1-12 | 111 | 130 |
| 30 | IWVDAHTDINTPLTTTSGNL | Arg1-13 | 121 | 140 |
| 31 | TPLTTTSGNLHGQPVSFLLK | Arg1-14 | 131 | 150 |
| 32 | HGQPVSFLLKELKGKIPDVP | Arg1-15 | 141 | 160 |
| 33 | ELKGKIPDVPGFSWVTPCIS | Arg1-16 | 151 | 170 |
| 34 | GFSWVTPCISAKDIVYIGLR | Arg1-17 | 161 | 180 |
| 35 | AKDIVYIGLRDVDPGEHYIL | Arg1-18 | 171 | 190 |
| 36 | DVDPGEHYILKTLGIKYFSM | Arg1-19 | 181 | 200 |
| 37 | KTLGIKYFSMTEVDRLGIGK | Arg1-20 | 191 | 210 |
| 38 | TEVDRLGIGKVMEETLSYLL | Arg1-21 | 201 | 220 |
| 39 | VMEETLSYLLGRKKRPIHLS | Arg1-22 | 211 | 230 |
| 40 | GRKKRPIHLSFDVDGLDPSF | Arg1-23 | 221 | 240 |
| 41 | FDVDGLDPSFTPATGTPVVG | Arg1-24 | 231 | 250 |
| 42 | TPATGTPVVGGLTYREGLYI | Arg1-25 | 241 | 260 |
| 43 | GLTYREGLYITEEIYKTGLL | Arg1-26 | 251 | 270 |
| 44 | TEEIYKTGLLSGLDIMEVNP | Arg1-27 | 261 | 280 |
| 45 | SGLDIMEVNPSLGKTPEEVT | Arg1-28 | 271 | 290 |
| 46 | SLGKTPEEVTRTVNTAVAIT | Arg1-29 | 281 | 300 |

TABLE A-continued

| SEQ ID NO | Sequence | Name | Start pos | End pos |
|---|---|---|---|---|
| 47 | RTVNTAVAITLACFGLAREG | Arg1-30 | 291 | 310 |
| 48 | LACFGLAREGNHKPIDYLNPPK | Arg1-31 | 301 | 322 |
| 49 | GLYITEEIYKTGLLSGLDIM | | 257 | 276 |
| 50 | GFSWVTPCISAKDIVYIGLRDVDPGEHYIL | | 161 | 190 |
| 51 | DVDPGEHYILKTLGIKYFSMTEVDRLGIGK | | 181 | 210 |
| 52 | GFSWVTPCISAKDIVYIGLRDVDPGEHYILKTLGIKYFSMTEVDRLGIGK | | 161 | 210 |
| 53 | KDIVYIGL | mARG1 | 172 | 179 |
| 54 | LGIKYFSM | mARG2 | 193 | 200 |
| 55 | DVDPGEHYIIKTLGIKYFSM* | | 181 | 200 |
| 56 | KTLGIKYFSMTEVDKLGIGK* | mARG20 | 191 | 210 |
| 57 | GFSWVTPCISAKDIVYIGLRDVDPGEHYIIKTLGIKYFSMTEVDKLGIGK* | | 161 | 210 |
| 58 | GFSWIKPCISSASIVYIGLRDVDPPEHFILKNYDIQYFSMRDIDRLGIQK# | | | |

*indicates a sequence from murine Arginase 1 which includes at least one difference relative to the corresponding region of human Arginase1. Residues which are non-identical with the corresponding human sequence are bold and underlined. Murine and human Arginase 1 are the same length so start and end positions are the same.
indicates a sequence from human Arginase 2. Start and end positions are the corresponding positions in human Arginase 1.

Alternative human Arginase 1 sequence (SEQ ID NO: 61)
MSAKSRTIGIIGAPFSKGQPRGGVEEGPTVLRAGLLEKLKEQECDVKDYGDLPFADIPN
DSPFQIVKNPRSVGKASEQLAGKVAEVKKNGRISLVLGGDHSLAISIGHARVHPDLGV
IWVDAHTDINTPLTTTSGNLHGQPVSFLLKELKGKIPDVPGFSWVTPCISAKDIVYIGLR
DVDPGEHYILKTLGIKYFSMTEVDRLGIGKVMEETLSYLLGRKRPIHLSFDVDGLDPSF
TPATGTPVVGGLTYREGLYITEEIYKTGLLSGLDIMEVNPSLGKTPEEVTRTVNTAVAIT
LACFGLAREGNHKPIDYLNPPK

The invention claimed is:

1. An isolated, immunogenic polypeptide fragment of a human Arginase protein of SEQ ID NO: 1 (Arginase 1) or SEQ ID NO: 60 (Arginase 2), wherein
    (a) the fragment of a human Arginase 1 protein is up to 55 amino acids in length and comprises the amino acid sequence of SEQ ID NO: 36 or SEQ ID NO: 53, or
    (b) the fragment of a human Arginase 2 protein is 8 to 55 amino acids in length and comprises at least 8 consecutive amino acids of SEQ ID NO: 58.

2. The polypeptide fragment of claim 1, which is a fragment of a human Arginase 1 protein and comprises the amino acid sequence of any one of SEQ ID NOs: 4-6, 9, 13, 15, 17, 31-39 or 50-54.

3. The polypeptide fragment of claim 1, which comprises at least 8, 9, 10, 15 or all 20 consecutive amino acids of any one of SEQ ID NOs: 37, 36, 34 or 35.

4. The polypeptide fragment of claim 1, wherein:
    a. the C terminal amino acid is replaced with the corresponding amide; and/or
    b. the fragment comprises an amino acid corresponding to position 190 of SEQ ID NO: 1 and the L at the position corresponding to position 190 of SEQ ID NO: 1 is replaced with I; and/or
    c. the fragment comprises an amino acid corresponding to position 205 of SEQ ID NO: 1 and the R at the position corresponding to position 205 of SEQ ID NO: 1 is replaced with K; and/or
    d. at least one additional moiety is attached to the N and/or C terminus of the fragment to improve solubility or manufacturability of the polypeptide fragment; and/or
    e. said fragment lacks or has reduced arginase activity relative to the corresponding full length arginase; and/or
    f. said fragment is capable of stimulating T cells which recognize cells expressing the corresponding arginase.

5. A composition comprising the polypeptide fragment of claim 1 and a pharmaceutically acceptable diluent or carrier.

6. The composition of claim 5, which further comprises an adjuvant selected from the group consisting of bacterial DNA based adjuvants, oil/surfactant based adjuvants, viral dsRNA based adjuvants, imidazochinilines, and a Montanide ISA adjuvant.

7. A method of treating or preventing a disease or condition in a subject, the method comprising administering to the subject an isolated, immunogenic polypeptide fragment of a human Arginase protein of SEQ ID NO: 1 (Arginase 1) or SEQ ID NO: 60 (Arginase 2), or a composition comprising the isolated polypeptide fragment and a pharmaceutically acceptable diluent or carrier, wherein:
    (a) the fragment of a human Arginase 1 protein is up to 55 amino acids in length and comprises the amino acid sequence of SEQ ID NO: 36 or SEQ ID NO: 53, or
    (b) the fragment of a human Arginase 2 protein is 8 to 55 amino acids in length and comprises at least 8 consecutive amino acids of SEQ ID NO: 58.

8. The method of claim 7, wherein the disease or condition is characterized at least in part by inappropriate or excessive immune suppressive function of an Arginase, and/or said disease or condition is cancer.

9. The method of claim 8, wherein the disease or condition is cancer and the method further comprises the simultaneous or sequential administration of an additional cancer therapy.

10. The method of claim 9, wherein the additional cancer therapy is one or more of Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

11. The method of claim 7, wherein the polypeptide fragment is a fragment of a human Arginase 1 protein and comprises the amino acid sequence of any one of SEQ ID NOs: 4-6, 9, 13, 15, 17, 31-39 or 50-54.

12. The method of claim 7, wherein the polypeptide fragment comprises at least 8, 9, 10, 15 or all 20 consecutive amino acids of any one of SEQ ID NOs: 37, 36, 34 or 35.

13. The method of claim 7, wherein:
a. the C terminal amino acid of the polypeptide fragment is replaced with the corresponding amide; and/or
b. the fragment comprises an amino acid corresponding to position 190 of SEQ ID NO: 1 and the L at the position corresponding to position 190 of SEQ ID NO: 1 of the polypeptide fragment is replaced with I; and/or
c. the fragment comprises an amino acid corresponding to position 205 of SEQ ID NO: 1 and the R at the position corresponding to position 205 of SEQ ID NO: 1 of the polypeptide fragment is replaced with K; and/or
d. at least one additional moiety is attached to the N and/or C terminus of the polypeptide fragment to improve solubility or manufacturability of the polypeptide fragment; and/or
e. the polypeptide fragment lacks or has reduced arginase activity relative to the corresponding full length arginase; and/or
f. the polypeptide fragment is capable of stimulating T cells which recognize cells expressing the corresponding arginase.

14. The method of claim 7, which comprises administering to the subject a composition comprising said polypeptide fragment and an adjuvant selected from the group consisting of bacterial DNA based adjuvants, oil/surfactant based adjuvants, viral dsRNA based adjuvants, imidazochinilines, and a Montanide ISA adjuvant.

15. A nucleic acid sequence encoding the immunogenic polypeptide fragment of claim 1.

16. A vector comprising the nucleic acid sequence of claim 15.

17. A method of treating or preventing a disease or condition in a subject, which method comprises administering to a subject in need thereof a composition comprising the nucleic acid sequence of claim 15 and a pharmaceutically acceptable carrier.

18. The method of claim 17, wherein the disease or condition is characterized by inappropriate or excessive immune suppressive function of an Arginase, and/or the disease or condition is cancer.

19. A method of treating or preventing a disease or condition in a subject, which method comprises administering to a subject in need thereof a composition comprising the vector of claim 16 and a pharmaceutically acceptable carrier.

20. The method of claim 19, wherein the disease or condition is characterized by inappropriate or excessive immune suppressive function of an Arginase, and/or the disease or condition is cancer.

21. The polypeptide fragment of claim 3, which comprises SEQ ID NO: 34 except that the cysteine in SEQ ID NO: 34 is replaced by a conservative amino acid substitution.

22. The polypeptide fragment of claim 4, wherein at least one additional moiety is attached to the N and/or C terminus to improve solubility or manufacturability of the polypeptide fragment, and wherein said additional moiety is a hydrophilic amino acid.

23. The polypeptide fragment of claim 22, wherein said hydrophilic amino acid is R or K.

24. The composition of claim 5, further comprising an adjuvant.

25. The method according to claim 9, wherein the additional cancer therapy is a cytokine therapy, a T-cell therapy, an NK therapy, an immune system checkpoint inhibitor, chemotherapy, radiotherapy, immunostimulating substances, gene therapy, or dendritic cells.

26. The method according to claim 25, wherein the immune system checkpoint inhibitor is an antibody.

27. The method of claim 12, wherein the polypeptide fragment comprises SEQ ID NO: 34 except that the cysteine in SEQ ID NO: 34 is replaced by a conservative amino acid substitution.

28. The method of claim 13, wherein at least one additional moiety is attached to the N and/or C terminus of the polypeptide fragment to improve solubility or manufacturability of the polypeptide fragment, and wherein said additional moiety is a hydrophilic amino acid.

29. The method of claim 28, wherein said hydrophilic amino acid is R or K.

* * * * *

SEQUENCE LISTING

<160> NUMBER OF SEQ ID NOS: 62

<210> SEQ ID NO 1
<211> LENGTH: 322
<212> TYPE: PRT
<213> ORGANISM: Homo sapiens

<400> SEQUENCE: 1

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
            85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
290                 295                 300

Gly Leu Ala Arg Glu Gly Asn His Lys Pro Ile Asp Tyr Leu Asn Pro
305                 310                 315                 320

Pro Lys

<210> SEQ ID NO 2
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 2

Gln Leu Ala Gly Lys Val Ala Glu Val
1               5

<210> SEQ ID NO 3
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 3

Leu Val Leu Gly Gly Asp His Ser Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 4

```
Leu Leu Lys Glu Leu Lys Gly Lys Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 5

Glu Leu Lys Gly Lys Ile Pro Asp Val
1               5

<210> SEQ ID NO 6
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 6

Val Met Glu Glu Thr Leu Ser Tyr Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 7

His Leu Ser Phe Asp Val Asp Gly Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 8

Ser Leu Gly Lys Thr Pro Glu Glu Val
1               5

<210> SEQ ID NO 9
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 9

Ile Val Tyr Ile Gly Leu Arg Asp Val
1               5

<210> SEQ ID NO 10
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 10
```

Gly Leu Leu Ser Gly Leu Asp Ile Met
1               5

<210> SEQ ID NO 11
<211> LENGTH: 9
<212> TYPE: PRT
<213> ORGANISM: Artificial Sequence
<220> FEATURE:
<223> OTHER INFORMATION: Peptide fragment of human Arginase 1

<400> SEQUENCE: 11

Asp Ile Met Glu Val Asn Pro Ser Leu
1               5

<210> SEQ ID NO 12
<211> LENGTH: 10
<212> TYPE: PRT
<213> ORGANISM: Artificial Sequence
<220> FEATURE:
<223> OTHER INFORMATION: Peptide fragment of human Arginase 1

<400> SEQUENCE: 12

Leu Leu Ser Gly Leu Asp Ile Met Glu Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Peptide fragment of human Arginase 1

<400> SEQUENCE: 13

Asn Leu His Gly Gln Pro Val Ser Phe Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Peptide fragment of human Arginase 1

<400> SEQUENCE: 14

Ser Leu Val Leu Gly Gly Asp His Ser Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Peptide fragment of human Arginase 1

<400> SEQUENCE: 15

Tyr Leu Leu Gly Arg Lys Lys Arg Pro Ile
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Peptide fragment of human Arginase 1

<400> SEQUENCE: 16

Val Leu Gly Gly Asp His Ser Leu Ala Ile

<210> SEQ ID NO 17
<211> LENGTH: 10
<212> TYPE: PRT
<213> ORGANISM: Artificial Sequence
<220> FEATURE:
<223> OTHER INFORMATION: Peptide fragment of human Arginase 1

<400> SEQUENCE: 17

Phe Leu Leu Lys Glu Leu Lys Gly Lys Ile
1               5                   10

<210> SEQ ID NO 18
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 18

Met Ser Ala Lys Ser Arg Thr Ile Gly Ile Ile Gly Ala Pro Phe Ser
1               5                   10                  15

Lys Gly Gln Pro
            20

<210> SEQ ID NO 19
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 19

Ile Gly Ala Pro Phe Ser Lys Gly Gln Pro Arg Gly Gly Val Glu Glu
1               5                   10                  15

Gly Pro Thr Val
            20

<210> SEQ ID NO 20
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 20

Arg Gly Gly Val Glu Glu Gly Pro Thr Val Leu Arg Lys Ala Gly Leu
1               5                   10                  15

Leu Glu Lys Leu
            20

<210> SEQ ID NO 21
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 21

Leu Arg Lys Ala Gly Leu Leu Glu Lys Leu Lys Glu Gln Glu Cys Asp
1               5                   10                  15

Val Lys Asp Tyr
            20

```
<210> SEQ ID NO 22
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 22

Lys Glu Gln Glu Cys Asp Val Lys Asp Tyr Gly Asp Leu Pro Phe Ala
1               5                   10                  15

Asp Ile Pro Asn
            20

<210> SEQ ID NO 23
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 23

Gly Asp Leu Pro Phe Ala Asp Ile Pro Asn Asp Ser Pro Phe Gln Ile
1               5                   10                  15

Val Lys Asn Pro
            20

<210> SEQ ID NO 24
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 24

Asp Ser Pro Phe Gln Ile Val Lys Asn Pro Arg Ser Val Gly Lys Ala
1               5                   10                  15

Ser Glu Gln Leu
            20

<210> SEQ ID NO 25
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 25

Arg Ser Val Gly Lys Ala Ser Glu Gln Leu Ala Gly Lys Val Ala Glu
1               5                   10                  15

Val Lys Lys Asn
            20

<210> SEQ ID NO 26
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 26

Ala Gly Lys Val Ala Glu Val Lys Lys Asn Gly Arg Ile Ser Leu Val
1               5                   10                  15

Leu Gly Gly Asp
            20
```

```
<210> SEQ ID NO 27
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 27

Gly Arg Ile Ser Leu Val Leu Gly Gly Asp His Ser Leu Ala Ile Gly
1               5                   10                  15

Ser Ile Ser Gly
            20

<210> SEQ ID NO 28
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 28

His Ser Leu Ala Ile Gly Ser Ile Ser Gly His Ala Arg Val His Pro
1               5                   10                  15

Asp Leu Gly Val
            20

<210> SEQ ID NO 29
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 29

His Ala Arg Val His Pro Asp Leu Gly Val Ile Trp Val Asp Ala His
1               5                   10                  15

Thr Asp Ile Asn
            20

<210> SEQ ID NO 30
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 30

Ile Trp Val Asp Ala His Thr Asp Ile Asn Thr Pro Leu Thr Thr Thr
1               5                   10                  15

Ser Gly Asn Leu
            20

<210> SEQ ID NO 31
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 31

Thr Pro Leu Thr Thr Thr Ser Gly Asn Leu His Gly Gln Pro Val Ser
1               5                   10                  15

Phe Leu Leu Lys
```

20

<210> SEQ ID NO 32
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 32

His Gly Gln Pro Val Ser Phe Leu Leu Lys Glu Leu Lys Gly Lys Ile
1               5                   10                  15

Pro Asp Val Pro
            20

<210> SEQ ID NO 33
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 33

Glu Leu Lys Gly Lys Ile Pro Asp Val Pro Gly Phe Ser Trp Val Thr
1               5                   10                  15

Pro Cys Ile Ser
            20

<210> SEQ ID NO 34
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 34

Gly Phe Ser Trp Val Thr Pro Cys Ile Ser Ala Lys Asp Ile Val Tyr
1               5                   10                  15

Ile Gly Leu Arg
            20

<210> SEQ ID NO 35
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 35

Ala Lys Asp Ile Val Tyr Ile Gly Leu Arg Asp Val Asp Pro Gly Glu
1               5                   10                  15

His Tyr Ile Leu
            20

<210> SEQ ID NO 36
<211> LENGTH: 20
<212> TYPE: PRT
<213> ORGANISM: Artificial Sequence
<220> FEATURE:
<223> OTHER INFORMATION: Peptide frgment of human Arginase 1

<400> SEQUENCE: 36

Asp Val Asp Pro Gly Glu His Tyr Ile Leu Lys Thr Leu Gly Ile Lys
1               5                   10                  15

```
Tyr Phe Ser Met
            20

<210> SEQ ID NO 37
<211> LENGTH: 20
<212> TYPE: PRT
<213> ORGANISM: Artificial Sequence
<220> FEATURE:
<223> OTHER INFORMATION: Peptide frgment of human Arginase 1

<400> SEQUENCE: 37

Lys Thr Leu Gly Ile Lys Tyr Phe Ser Met Thr Glu Val Asp Arg Leu
1               5                   10                  15

Gly Ile Gly Lys
            20

<210> SEQ ID NO 38
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 38

Thr Glu Val Asp Arg Leu Gly Ile Gly Lys Val Met Glu Glu Thr Leu
1               5                   10                  15

Ser Tyr Leu Leu
            20

<210> SEQ ID NO 39
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 39

Val Met Glu Glu Thr Leu Ser Tyr Leu Leu Gly Arg Lys Lys Arg Pro
1               5                   10                  15

Ile His Leu Ser
            20

<210> SEQ ID NO 40
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 40

Gly Arg Lys Lys Arg Pro Ile His Leu Ser Phe Asp Val Asp Gly Leu
1               5                   10                  15

Asp Pro Ser Phe
            20

<210> SEQ ID NO 41
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 41

Phe Asp Val Asp Gly Leu Asp Pro Ser Phe Thr Pro Ala Thr Gly Thr
1               5                   10                  15
```

Pro Val Val Gly
        20

<210> SEQ ID NO 42
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 42

Thr Pro Ala Thr Gly Thr Pro Val Val Gly Gly Leu Thr Tyr Arg Glu
1               5                   10                  15

Gly Leu Tyr Ile
        20

<210> SEQ ID NO 43
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 43

Gly Leu Thr Tyr Arg Glu Gly Leu Tyr Ile Thr Glu Glu Ile Tyr Lys
1               5                   10                  15

Thr Gly Leu Leu
        20

<210> SEQ ID NO 44
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 44

Thr Glu Glu Ile Tyr Lys Thr Gly Leu Leu Ser Gly Leu Asp Ile Met
1               5                   10                  15

Glu Val Asn Pro
        20

<210> SEQ ID NO 45
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 45

Ser Gly Leu Asp Ile Met Glu Val Asn Pro Ser Leu Gly Lys Thr Pro
1               5                   10                  15

Glu Glu Val Thr
        20

<210> SEQ ID NO 46
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 46

Ser Leu Gly Lys Thr Pro Glu Glu Val Thr Arg Thr Val Asn Thr Ala

```
1               5                   10                  15

Val Ala Ile Thr
            20

<210> SEQ ID NO 47
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 47

Arg Thr Val Asn Thr Ala Val Ala Ile Thr Leu Ala Cys Phe Gly Leu
1               5                   10                  15

Ala Arg Glu Gly
            20

<210> SEQ ID NO 48
<211> LENGTH: 22
<212> TYPE: PRT
<213> ORGANISM: Artificial Sequence
<220> FEATURE:
<223> OTHER INFORMATION: Peptide frgment of human Arginase 1

<400> SEQUENCE: 48

Leu Ala Cys Phe Gly Leu Ala Arg Glu Gly Asn His Lys Pro Ile Asp
1               5                   10                  15

Tyr Leu Asn Pro Pro Lys
            20

<210> SEQ ID NO 49
<211> LENGTH: 20
<212> TYPE: PRT
<213> ORGANISM: Artificial Sequence
<220> FEATURE:
<223> OTHER INFORMATION: Peptide fragment of human Arginase 1

<400> SEQUENCE: 49

Gly Leu Tyr Ile Thr Glu Glu Ile Tyr Lys Thr Gly Leu Leu Ser Gly
1               5                   10                  15

Leu Asp Ile Met
            20

<210> SEQ ID NO 50
<211> LENGTH: 30
<212> TYPE: PRT
<213> ORGANISM: Artificial Sequence
<220> FEATURE:
<223> OTHER INFORMATION: Peptide fragment of human Arginase 1

<400> SEQUENCE: 50

Gly Phe Ser Trp Val Thr Pro Cys Ile Ser Ala Lys Asp Ile Val Tyr
1               5                   10                  15

Ile Gly Leu Arg Asp Val Asp Pro Gly Glu His Tyr Ile Leu
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Peptide fragment of human Arginase 1

<400> SEQUENCE: 51
```

```
Asp Val Asp Pro Gly Glu His Tyr Ile Leu Lys Thr Leu Gly Ile Lys
1               5                   10                  15

Tyr Phe Ser Met Thr Glu Val Asp Arg Leu Gly Ile Gly Lys
            20                  25                  30

<210> SEQ ID NO 52
<211> LENGTH: 50
<212> TYPE: PRT
<213> ORGANISM: Artificial Sequence
<220> FEATURE:
<223> OTHER INFORMATION: Peptide fragment of human Arginase 1

<400> SEQUENCE: 52

Gly Phe Ser Trp Val Thr Pro Cys Ile Ser Ala Lys Asp Ile Val Tyr
1               5                   10                  15

Ile Gly Leu Arg Asp Val Asp Pro Gly Glu His Tyr Ile Leu Lys Thr
            20                  25                  30

Leu Gly Ile Lys Tyr Phe Ser Met Thr Glu Val Asp Arg Leu Gly Ile
        35                  40                  45

Gly Lys
    50

<210> SEQ ID NO 53
<211> LENGTH: 8
<212> TYPE: PRT
<213> ORGANISM: Artificial Sequence
<220> FEATURE:
<223> OTHER INFORMATION: Peptide fragment of human Arginase 1

<400> SEQUENCE: 53

Lys Asp Ile Val Tyr Ile Gly Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Peptide fragment of human Arginase 1

<400> SEQUENCE: 54

Leu Gly Ile Lys Tyr Phe Ser Met
1               5

<210> SEQ ID NO 55
<211> LENGTH: 20
<212> TYPE: PRT
<213> ORGANISM: Artificial Sequence
<220> FEATURE:
<223> OTHER INFORMATION: Peptide fragment of murine Arginase 1

<400> SEQUENCE: 55

Asp Val Asp Pro Gly Glu His Tyr Ile Ile Lys Thr Leu Gly Ile Lys
1               5                   10                  15

Tyr Phe Ser Met
            20

<210> SEQ ID NO 56
<211> LENGTH: 20
<212> TYPE: PRT
<213> ORGANISM: Artificial Sequence
<220> FEATURE:
<223> OTHER INFORMATION: Peptide fragment of murine Arginase 1

<400> SEQUENCE: 56
```

```
Lys Thr Leu Gly Ile Lys Tyr Phe Ser Met Thr Glu Val Asp Lys Leu
1               5                   10                  15

Gly Ile Gly Lys
            20

<210> SEQ ID NO 57
<211> LENGTH: 50
<212> TYPE: PRT
<213> ORGANISM: Artificial Sequence
<220> FEATURE:
<223> OTHER INFORMATION: Peptide fragment of murine Arginase 1

<400> SEQUENCE: 57

Gly Phe Ser Trp Val Thr Pro Cys Ile Ser Ala Lys Asp Ile Val Tyr
1               5                   10                  15

Ile Gly Leu Arg Asp Val Asp Pro Gly Glu His Tyr Ile Ile Lys Thr
            20                  25                  30

Leu Gly Ile Lys Tyr Phe Ser Met Thr Glu Val Asp Lys Leu Gly Ile
        35                  40                  45

Gly Lys
    50

<210> SEQ ID NO 58
<211> LENGTH: 50
<212> TYPE: PRT
<213> ORGANISM: Artificial Sequence
<220> FEATURE:
<223> OTHER INFORMATION: Peptide fragment of human Arginase 2

<400> SEQUENCE: 58

Gly Phe Ser Trp Ile Lys Pro Cys Ile Ser Ala Ser Ile Val Tyr
1               5                   10                  15

Ile Gly Leu Arg Asp Val Asp Pro Pro Glu His Phe Ile Leu Lys Asn
            20                  25                  30

Tyr Asp Ile Gln Tyr Phe Ser Met Arg Asp Ile Asp Arg Leu Gly Ile
        35                  40                  45

Gln Lys
    50

<210> SEQ ID NO 59
<211> LENGTH: 323
<212> TYPE: PRT
<213> ORGANISM: Mus musculus

<400> SEQUENCE: 59

Met Ser Ser Lys Pro Lys Ser Leu Glu Ile Ile Gly Ala Pro Phe Ser
1               5                   10                  15

Lys Gly Gln Pro Arg Gly Gly Val Glu Lys Gly Pro Ala Ala Leu Arg
            20                  25                  30

Lys Ala Gly Leu Leu Glu Lys Leu Lys Glu Thr Glu Tyr Asp Val Arg
        35                  40                  45

Asp His Gly Asp Leu Ala Phe Val Asp Val Pro Asn Asp Ser Ser Phe
    50                  55                  60

Gln Ile Val Lys Asn Pro Arg Ser Val Gly Lys Ala Asn Glu Glu Leu
65                  70                  75                  80

Ala Gly Val Val Ala Glu Val Gln Lys Asn Gly Arg Val Ser Val Val
                85                  90                  95

Leu Gly Gly Asp His Ser Leu Ala Val Gly Ser Ile Ser Gly His Ala
            100                 105                 110
```

```
Arg Val His Pro Asp Leu Cys Val Ile Trp Val Asp Ala His Thr Asp
            115                 120                 125
Ile Asn Thr Pro Leu Thr Thr Ser Ser Gly Asn Leu His Gly Gln Pro
130                 135                 140
Val Ser Phe Leu Leu Lys Glu Leu Lys Gly Lys Phe Pro Asp Val Pro
145                 150                 155                 160
Gly Phe Ser Trp Val Thr Pro Cys Ile Ser Ala Lys Asp Ile Val Tyr
                    165                 170                 175
Ile Gly Leu Arg Asp Val Asp Pro Gly Glu His Tyr Ile Ile Lys Thr
                180                 185                 190
Leu Gly Ile Lys Tyr Phe Ser Met Thr Glu Val Asp Lys Leu Gly Ile
                195                 200                 205
Gly Lys Val Met Glu Glu Thr Phe Ser Tyr Leu Leu Gly Arg Lys Lys
            210                 215                 220
Arg Pro Ile His Leu Ser Phe Asp Val Asp Gly Leu Asp Pro Ala Phe
225                 230                 235                 240
Thr Pro Ala Thr Gly Thr Pro Val Leu Gly Gly Leu Ser Tyr Arg Glu
                    245                 250                 255
Gly Leu Tyr Ile Thr Glu Glu Ile Tyr Lys Thr Gly Leu Leu Ser Gly
                260                 265                 270
Leu Asp Ile Met Glu Val Asn Pro Thr Leu Gly Lys Thr Ala Glu Glu
                275                 280                 285
Val Lys Ser Thr Val Asn Thr Ala Val Ala Leu Thr Leu Ala Cys Phe
            290                 295                 300
Gly Thr Gln Arg Glu Gly Asn His Lys Pro Gly Thr Asp Tyr Leu Lys
305                 310                 315                 320
Pro Pro Lys

<210> SEQ ID NO 60
<211> LENGTH: 354
<212> TYPE: PRT
<213> ORGANISM: Homo sapiens

<400> SEQUENCE: 60

Met Ser Leu Arg Gly Ser Leu Ser Arg Leu Leu Gln Thr Arg Val His
1               5                   10                  15
Ser Ile Leu Lys Lys Ser Val His Ser Val Ala Val Ile Gly Ala Pro
                20                  25                  30
Phe Ser Gln Gly Gln Lys Arg Lys Gly Val Glu His Gly Pro Ala Ala
            35                  40                  45
Ile Arg Glu Ala Gly Leu Met Lys Arg Leu Ser Ser Leu Gly Cys His
        50                  55                  60
Leu Lys Asp Phe Gly Asp Leu Ser Phe Thr Pro Val Pro Lys Asp Asp
65                  70                  75                  80
Leu Tyr Asn Asn Leu Ile Val Asn Pro Arg Ser Val Gly Leu Ala Asn
                85                  90                  95
Gln Glu Leu Ala Glu Val Val Ser Arg Ala Val Ser Asp Gly Tyr Ser
            100                 105                 110
Cys Val Thr Leu Gly Gly Asp His Ser Leu Ala Ile Gly Thr Ile Ser
        115                 120                 125
Gly His Ala Arg His Cys Pro Asp Leu Cys Val Val Trp Val Asp Ala
    130                 135                 140
His Ala Asp Ile Asn Thr Pro Leu Thr Thr Ser Ser Gly Asn Leu His
145                 150                 155                 160
```

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Pro Glu His Phe Ile
        195                 200                 205

Leu Lys Asn Tyr Asp Ile Gln Tyr Phe Ser Met Arg Asp Ile Asp Arg
    210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
        275                 280                 285

Leu Ser Ala Leu Asp Leu Val Glu Val Asn Pro Gln Leu Ala Thr Ser
    290                 295                 300

Glu Glu Glu Ala Lys Thr Thr Ala Asn Leu Ala Val Asp Val Ile Ala
305                 310                 315                 320

Ser Ser Phe Gly Gln Thr Arg Glu Gly Gly His Ile Val Tyr Asp Gln
                325                 330                 335

Leu Pro Thr Pro Ser Ser Pro Asp Glu Ser Glu Asn Gln Ala Arg Val
            340                 345                 350

Arg Ile

<210> SEQ ID NO 61
<211> LENGTH: 318
<212> TYPE: PRT
<213> ORGANISM: Homo sapiens

<400> SEQUENCE: 61

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Ala Gly Leu Leu Glu Lys Leu Lys Glu Gln Glu Cys Asp Val Lys Asp
        35                  40                  45

Tyr Gly Asp Leu Pro Phe Ala Asp Ile Pro Asn Asp Ser Pro Phe Gln
    50                  55                  60

Ile Val Lys Asn Pro Arg Ser Val Gly Lys Ala Ser Glu Gln Leu Ala
65                  70                  75                  80

Gly Lys Val Ala Glu Val Lys Lys Asn Gly Arg Ile Ser Leu Val Leu
                85                  90                  95

Gly Gly Asp His Ser Leu Ala Ile Ser Ile Gly His Ala Arg Val His
            100                 105                 110

Pro Asp Leu Gly Val Ile Trp Val Asp Ala His Thr Asp Ile Asn Thr
        115                 120                 125

Pro Leu Thr Thr Thr Ser Gly Asn Leu His Gly Gln Pro Val Ser Phe
    130                 135                 140

Leu Leu Lys Glu Leu Lys Gly Lys Ile Pro Asp Val Pro Gly Phe Ser
145                 150                 155                 160

Trp Val Thr Pro Cys Ile Ser Ala Lys Asp Ile Val Tyr Ile Gly Leu
                165                 170                 175

```
Arg Asp Val Asp Pro Gly Glu His Tyr Ile Leu Lys Thr Leu Gly Ile
            180             185                 190

Lys Tyr Phe Ser Met Thr Glu Val Asp Arg Leu Gly Ile Gly Lys Val
            195             200                 205

Met Glu Glu Thr Leu Ser Tyr Leu Leu Gly Arg Lys Arg Pro Ile His
            210             215                 220

Leu Ser Phe Asp Val Asp Gly Leu Asp Pro Ser Phe Thr Pro Ala Thr
225             230                 235                 240

Gly Thr Pro Val Val Gly Gly Leu Thr Tyr Arg Glu Gly Leu Tyr Ile
                245             250                 255

Thr Glu Glu Ile Tyr Lys Thr Gly Leu Leu Ser Gly Leu Asp Ile Met
            260             265                 270

Glu Val Asn Pro Ser Leu Gly Lys Thr Pro Glu Glu Val Thr Arg Thr
            275             280                 285

Val Asn Thr Ala Val Ala Ile Thr Leu Ala Cys Phe Gly Leu Ala Arg
            290             295                 300

Glu Gly Asn His Lys Pro Ile Asp Tyr Leu Asn Pro Pro Lys
305             310                 315

<210> SEQ ID NO 62
<211> LENGTH: 8
<212> TYPE: PRT
<213> ORGANISM: Artificial Sequence
<220> FEATURE:
<223> OTHER INFORMATION: Additional amino acids of isoform 1 of human
      Arginase 1

<400> SEQUENCE: 62

Val Thr Gln Asn Phe Leu Ile Leu
1               5
```